(12) United States Patent
Doherty et al.

(10) Patent No.: US 7,563,816 B2
(45) Date of Patent: Jul. 21, 2009

(54) OPHTHALMIC COMPOSITIONS FOR TREATING OCULAR HYPERTENSION

(75) Inventors: James B. Doherty, Montvale, NJ (US); Dong-Ming Shen, Edison, NJ (US)

(73) Assignee: Merck & Co. Inc., Rahway, NJ (US)

( * ) Notice: Subject to any disclaimer, the term of this patent is extended or adjusted under 35 U.S.C. 154(b) by 219 days.

(21) Appl. No.: 11/630,172

(22) PCT Filed: Jul. 15, 2005

(86) PCT No.: PCT/US2005/025136

§ 371 (c)(1), (2), (4) Date: Dec. 19, 2006

(87) PCT Pub. No.: WO2006/020003

PCT Pub. Date: Feb. 23, 2006

(65) Prior Publication Data

US 2008/0032951 A1 Feb. 7, 2008

Related U.S. Application Data

(60) Provisional application No. 60/589,444, filed on Jul. 20, 2004.

(51) Int. Cl.
*A61K 31/415* (2006.01)
*C07D 231/56* (2006.01)
(52) U.S. Cl. .................. 514/403; 548/362.5
(58) Field of Classification Search .............. 548/362.5; 514/403
See application file for complete search history.

(56) References Cited

U.S. PATENT DOCUMENTS

| | | | |
|---|---|---|---|
| 3,586,694 A | 6/1971 | Shen et al. | |
| 4,690,931 A | 9/1987 | Wick et al. | |
| 5,151,444 A | 9/1992 | Ueno et al. | |
| 5,296,504 A | 3/1994 | Stjernschantz et al. | |
| 5,352,708 A | 10/1994 | Woodward et al. | |
| 5,422,368 A | 6/1995 | Stjernschantz et al. | |
| 5,573,758 A | 11/1996 | Adorante et al. | |
| 5,889,052 A | 3/1999 | Klimko et al. | |
| 5,925,342 A | 7/1999 | Adorante et al. | |
| 6,030,999 A * | 2/2000 | Stjernschantz et al. | 514/530 |
| 6,956,036 B1 * | 10/2005 | May et al. | 514/233.8 |
| 7,053,085 B2 * | 5/2006 | Billot et al. | 514/228.8 |
| 7,196,082 B2 * | 3/2007 | Doherty et al. | 514/235.2 |

FOREIGN PATENT DOCUMENTS

| | | |
|---|---|---|
| EP | 1114816 | 7/2001 |
| WO | WO 8910757 | 11/1989 |
| WO | WO 9413275 | 6/1994 |
| WO | WO 9428900 | 12/1994 |
| WO | WO 9633719 | 10/1996 |
| WO | WO 0146140 | 6/2001 |
| WO | WO 01/70702 | 9/2001 |
| WO | WO 0172268 | 10/2001 |
| WO | WO 0224647 | 3/2002 |
| WO | WO 0242268 | 5/2002 |
| WO | WO 2004085431 | 10/2004 |

OTHER PUBLICATIONS

Billot et al., 2005, see CAS: 143:387049.*
May et al., 2001, CAS:135:257241.*
S. R. Moore et al., "Development and Aging of Cell Topography in the Human Retinal PIgment Epithelium", 1997, pp. 2016-2026, vol. 38, No. 10 Ophthalmology & Visual Science.
S. H. Wilen, "Chirality in Molecules Devoid of Chiral Centers" pp. 1119-1990, Sterochemistry of Organic Compounds.
S. M. Berge et al., "Pharmaceutical Salts", 1977, vol. 66, No. 1, J. of Pharmaceutical Sciences.
M. P. Cava et al., "Synthesis of 4-Demethoxy-6,11,-Dideoxydaunomycinone. A Highly Deoxygeneated Anthracyclinone" 1986, vol. 51, pp. 2044-2046, J. Org. Chem.
F. W. Lichtenthaler, "The Chemistry and Properties of Enol Phosphates", 1961, pp. 607-649, Chemical Review.
T. Hata et al., "Facile Synthesis of Unesterifed Enolphosphates", 1979, pp. 189-191, Communications.
A. F. Abdel-Magid et al., "Reductive Amination of Aldehydes and Ketones with Sodium Triacetoxyborohydride. Studies on Direct and Indirect Reductive Amination Procedures", 1996, pp. 3849-3862, vol. 61, J. Org. Chem.
Gaudry et al., "1-Bromo-3-Methyl-2-Butanone", 1988, pp. 193-195, Organic Syntheses.

* cited by examiner

*Primary Examiner*—Rei-tsang Shiao
(74) *Attorney, Agent, or Firm*—Sylvia A. Ayler; William Krovatin

(57) ABSTRACT

This invention relates to potent potassium channel blocker compounds of Formula (I) or a formulation thereof for the treatment of glaucoma and other conditions which leads to elevated intraoccular pressure in the eye of a patient. This invention also relates to the use of such compounds to provide a neuroprotective effect to the eye of mammalian species, particularly humans.

10 Claims, No Drawings

OPHTHALMIC COMPOSITIONS FOR TREATING OCULAR HYPERTENSION

This application claims the benefit of U.S. Provisional Application 60/589,444, filed Jul. 20, 2004.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of opthalmologists to represent merely the earliest phase in the onset of glaucoma.

There are several therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Opthalmol. Vis. Sci 38, 1997; WO 89/10757, WO 94/28900, and WO 96/33719).

Some Maxi-K channel blockers containing ketone functional groups have quite low aqueous solubility. This presents a serious problem when used to treat ocular diseases such as glaucoma because treatment is typically in the form of aqueous ophthalmic solution formulations.

SUMMARY OF THE INVENTION

This invention relates to the use of potent potassium channel blockers or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using novel enol phosphate compounds having structural formula I:

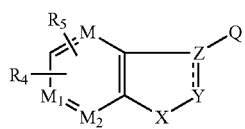

Formula I or a pharmaceutically acceptable salt, in vivo hydrolysable ester, enantiomer, diastereomer, geometric isomers or mixture thereof:

wherein,

M, M1, and M2, independently are CH or N;

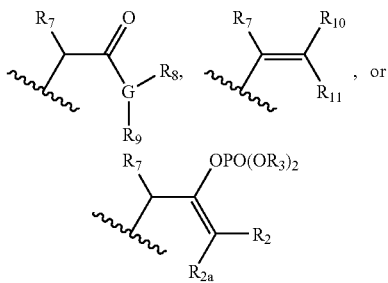

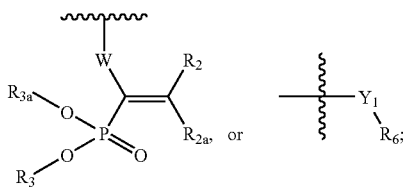

$R_{10}$ and $R_{11}$ represent $OPO(OR_3)_2$ and $R_6$, respectively or $R_6$ and $OPO(OR_3)_2$, respectively Q represents Z represents N or C;

when Z is N then the bond between Y and Z is a single bond and between X and Y respectively represents: $CR_1=N$; $CR_1=CR_1$; $CR_1=CR_1$; or $N=CR_1$;

when Z is C then X is O or S; Y represents $CR_1$ and the bond between Y and Z is a double bond as denoted by the dotted line ---, $R_1$ represents:

$R_{1'}$ represents hydrogen, $C_{1-6}$ alkyl, $-(CH_2)_nC_{3-8}$ cycloalkyl, said alkyl or cycloalkyl optionally substituted with 1-3 groups of Ra;

or when X-Y equals $CR_1=CR_{1'}$ or $CR_1=CR_1$, $R_1$ and $R_{1'}$ taken together with the intervening double bond can optionally form a 4-10 membered ring or fused ring optionally interrupted by 1-3 atoms of O, S, C(O) or NR, and optionally having 1-5 double bonds, and optionally substituted by 1-3 groups selected from $R^a$;

with the proviso that there is at least one enol phosphate group present on the compound, W represents $-(CHR_7)_p-$;

$Y_1$ represents $-(CH_2)_n-$, $-CO(CH_2)_n-$, $-SO_2-$, $-O-$, $-S-$, $-CH(OR^{\wedge})-$, or $CONR^{\wedge}$ $R^{\wedge}$ represents hydrogen, $C_{1-10}$ alkyl, $-(CH_2)_nC_{1-6}$ alkoxy, $-(CH_2)_nC_{3-8}$ cycloalkyl, $-(CH_2)_nC_{3-10}$ heterocyclyl, said alkyl, heterocyclyl, aryl or heteroaryl optionally substituted with 1-3 groups selected from $R^a$;

or, $R^{\wedge}$ and $R_6$ taken together with the intervening N atom of $CONR'$ of $Y_1$ to form a 4-10 membered carbocyclic or heterocyclic ring or fused ring optionally interrupted by 1-3 atoms of O, S, C(O) or NR, and optionally having 1-5 double bonds, and optionally substituted by 1-3 groups selected from $R^a$;

G represents N, CRy, or 0, wherein $R_8$ is absent when G is O;

$R_2$ and $R_{2a}$ independently represents hydrogen, $C_{1-10}$ alkyl, $-(CH_2)_nC_{3-8}$ cycloalkyl, $-(CH_2)_nC_{3-10}$ heterocyclyl, $-(CH_2)_nC_{6-10}$ aryl, $-(CH_2)_nC_{1-6}$ alkoxy, $CF_3$, nitro, OH, cyano or halogen, said alkyl, alkoxy, heterocyclyl, or aryl optionally substituted with 1-3 groups of $R^a$;

or, $R_2$ and $R_{2a}$ taken together with the intervening atom form a 4-10 membered cyclic carbon or heterocyclic ring or fused ring optionally interrupted by 1-2 atoms of O, S, C(O) or NR, and optionally having 1-5 double bonds, and optionally substituted by 1-3 groups selected from $R^a$;

$R_3$ and $R_{3a}$ independently represent hydrogen, $C_{1-10}$ alkyl, —$(CH_2)_nC_{3-10}$ heterocyclyl, —$(CH_2)_nC_{1-6}$ alkoxy, —$(CH_2)_nC_{6-10}$ aryl, said alkyl, alkoxy, heterocyclyl, or aryl optionally substituted with 1-3 groups of $R^a$;

$R_4$ and $R_5$ independently represent hydrogen, $C_{1-6}$ alkoxy, OH, $C_{1-6}$ alkyl, $C_{1-6}$ alkenyl, S(O)qR, COOR, COR, SO$_3$H, —O(CH$_2$)$_n$N(R)$_2$, —O(CH$_2$)$_n$CO$_2$R, —OPO(OH)$_2$, CF$_3$, OCF$_3$, —N(R)$_2$, nitro, cyano, $C_{1-6}$ alkylamino, or halogen;

$R_6$ represents hydrogen, $C_{1-10}$ alkyl, —(CH$_2$)$_n$C$_{6-10}$ aryl, —NH(CH$_2$)$_n$C$_{6-10}$ aryl, —(CH$_2$)$_n$C$_{5-10}$ heteroaryl, —NH(CH$_2$)$_n$C$_{5-10}$ heteroaryl, (C$_{6-10}$ aryl)O—, —(CH$_2$)$_n$C$_{3-10}$ heterocyclyl, —(CH$_2$)$_n$C$_{3-10}$ cycloalkyl including fused rings, —COOR, —C(O)CO$_2$R, said aryl, heteroaryl, heterocyclyl, cycloalkyl, and alkyl optionally substituted with 1-3 groups selected from $R^a$ $R_7$ represents hydrogen, $C_{1-6}$ alkyl, —(CH$_2$)$_n$COOR or —(CH$_2$)$_n$N(R)$_2$, $R_8$ represents hydrogen, $C_{1-10}$ alkyl, $C_{1-6}$ alkylSR, —(CH$_2$)$_n$—O(CH$_2$)$_m$OR, —(CH$_2$)$_n$C$_{1-6}$ alkoxy, —(CH$_2$)$_n$C$_{3-8}$ cycloalkyl, —(CH$_2$)$_n$C$_{3-10}$ heterocyclyl, —(CH$_2$)$_n$C$_{5-10}$ heteroaryl, —N(R)$_2$, —COOR, or —(CH$_2$)$_n$C$_{6-10}$ aryl, said alkyl, heterocyclyl, aryl or heteroaryl optionally substituted with 1-3 groups selected from $R^a$;

$R_9$ represents hydrogen, $C_{1-10}$ alkyl, —(CH$_2$)$_n$C$_{3-8}$ cycloalkyl, —(CH$_2$)$_n$C$_{3-10}$ heterocyclyl, —(CH$_2$)$_n$C$_{5-10}$ heteroaryl, —(CH$_2$)$_n$COOR, —(CH$_2$)$_n$C$_{6-10}$ aryl, —(CH$_2$)$_n$NHR$_8$, —(CH$_2$)$_n$N(R)$_2$, —(CH$_2$)$_n$N(R$_8$)$_2$, —(CH$_2$)$_n$NHCOOR, —(CH$_2$)$_n$N(R$_8$)CO$_2$R, —(CH$_2$)$_n$N(R$_8$)COR, —(CH$_2$)$_n$NHCOR, —(CH$_2$)$_n$CONH(R$_8$), aryl, —(CH$_2$)$_n$C$_{1-6}$—OR, CF$_3$, (CH$_2$)$_n$SO$_2$R, —(CH$_2$)$_n$SO$_2$N(R)$_2$, —(CH$_2$)$_n$CON(R)$_2$, —(CH$_2$)$_n$CONHC(R)$_3$, —(CH$_2$)$_n$CONHC(R)CO$_2$R, —(CH$_2$)$_n$COR$_8$, nitro, cyano or halogen, said alkyl, alkoxy, heterocyclyl, aryl or heteroaryl optionally substituted with 1-3 groups of Ra;

or, when Q is N, $R_8$ and $R_9$ taken together with the intervening N atom form a 4-10 membered heterocyclic carbon ring optionally interrupted by 1-2 atoms of O, S, C(O) or NR, and optionally having 1-5 double bonds, and optionally substituted by 1-3 groups selected from $R^a$;

or when Q is CRy, $R_8$ and $R_9$ taken together with the intervening C atom form a 3-10 membered carbocyclic ring or fused ring optionally interrupted by 1-2 atoms of O, S, C(O) or NR, and optionally having 1-5 double bonds, and optionally substituted by 1-3 groups selected from $R^a$;

or or when Q is CRy, $R_8$ and $R_9$ taken together with the intervening CRy form a 5-12 membered fused ring optionally interrupted by 1-3 atoms of O, S, C(O) or NR, and optionally having 1-5 double bonds, and optionally substituted by 1-3 groups selected from $R^a$;

$R_w$ represents H, $C_{1-6}$ alkyl, —C(O)C$_{1-6}$ alkyl, —C(O)OC$_{1-6}$ alkyl, —SO$_2$N(R)$_2$, —SO$_2$C$_{1-16}$ alkyl, —SO$_2$C$_{6-10}$ aryl, NO$_2$, CN or —C(O)N(R)$_2$;

R, Ry, and R* independently represent hydrogen, or $C_{1-6}$ alkyl;

$R^a$ represents F, Cl, Br, I, CF$_3$, N(R)$_2$, NO$_2$, CN, —COR$_8$, —CONHR$_8$, —CON(R$_8$)$_2$, —O(CH$_2$)$_n$COOR, —NH(CH$_2$)$_n$OR, —COOR, —OCF$_3$, —NHCOR, —SO$_2$R, —SO$_2$NR$_2$, —SR, (C$_1$-C$_6$ alkyl)O—, —(CH$_2$)$_n$—O—(CH$_2$)$_m$OR, —(CH$_2$)$_n$C$_{1-6}$ alkoxy, (aryl)O—, —(CH$_2$)$_n$OH, (C$_1$-C$_6$ alkyl)S(O)$_m$—, H$_2$N—C(NH)—, (C$_1$-C$_6$ alkyl)C(O)—, (C$_1$-C$_6$ alkyl)OC(O)NH—, —(C$_1$-C$_6$ alkyl) NR$_w$(CH$_2$)$_n$C$_{3-10}$ heterocyclyl-R$_w$, —(C$_1$-C$_6$ alkyl)O (CH$_2$)$_n$C$_{3-10}$ heterocyclyl-R$_w$, —(C$_1$-C$_6$ alkyl)S(CH$_2$)$_n$C$_{3-10}$ heterocyclyl-R$_w$, —(C$_1$-C$_6$ alkyl)-C$_{3-10}$ heterocyclyl-R$^w$, —(CH$_2$)$_n$—Z$^1$—C(=Z$^2$)N(R)$_2$, —(C$_{2-6}$ alkenyl) NR$_w$(CH$_2$)$_n$C$_{3-10}$ heterocyclyl-R$_w$, —(C$_{2-6}$ alkenyl)O (CH$_2$)$_n$C$_{3-10}$ heterocyclyl-R$_w$, —(C$_{2-6}$ alkenyl)S(CH$_2$)$_n$C$_{3-10}$ heterocyclyl-R$_w$, —(C$_{2-6}$ alkenyl)-C$_{3-10}$ heterocyclyl-R$_w$, —(C$_{2-6}$ alkenyl)—Z$^1$—C(=Z$^2$)N(R)$_2$, —(CH$_2$)$_n$SO$_2$R, —(CH$_2$)$_n$SO$_3$H, —(CH$_2$)$_n$PO(OR)$_2$, —(CH$_2$)$_n$OPO(OR)$_2$, C$_{3-10}$cycloalkyl, C$_{6-10}$ aryl, C$_{3-10}$ heterocyclyl, C$_{2-6}$ alkenyl, and C$_1$-C$_{10}$ alkyl, said alkyl, alkenyl, alkoxy, heterocyclyl and aryl optionally substituted with 1-3 groups selected from C$_1$-C$_6$ alkyl, CN, NO$_2$, OH, CON(R)$_2$ and COOR;

$Z^1$ and $Z^2$ independently represents NR$_w$, O, CH$_2$, or S;

m is 0-3;

n is 0-3;

p is 0-1; and q is 0-2.

These compounds have much higher aqueous solubility than the corresponding ketones from which these enol phosphates can be convered to. This and other aspects of the invention will be realized upon inspection of the invention as a whole.

DETAILED DESCRIPTION OF THE INVENTION

The present invention is directed to novel potassium channel blockers of Formula I. It also relates to a method for decreasing elevated intraocular pressure or treating glaucoma by administration, preferably topical or intra-camaral administration, of a composition containing a potassium channel blocker of Formula I described hereinabove and a pharmaceutically acceptable carrier.

One embodiment of this invention is realized when —X—Y— is CR$_1$=N— and all other variables are as originally described.

Another embodiment of this invention is realized when —X—Y— respectively is CR$_1$=CR$_5$ and all other variables are as originally described.

Another embodiment of this invention is realized when —X—Y— respectively is CR$_5$=CR$_1$ and all other variables are as originally described.

Another embodiment of this invention is realized when —X—Y— respectively is N=CR$_1$ and all other variables are as originally described.

Another embodiment of this invention is realized when M, M1, and M2 are CH and all other variables are as originally described.

Another embodiment of this invention is realized when at least one of M, M1, and M2 is N and the other(s) is CH and all other variables are as originally described.

Another embodiment of this invention is realized when Q represents

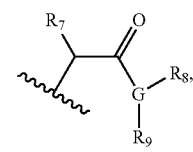

and all other variables are as originally described.

Another embodiment of this invention is realized when Q represents

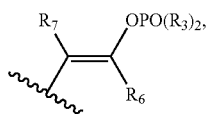

and all other variables are as originally described.

Another embodiment of this invention is realized when Q represents

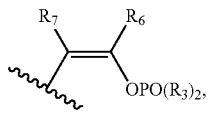

and all other variables are as originally described.

Another embodiment of this invention is realized when Q represents

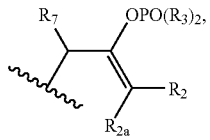

and all other variables are as originally described.

Another embodiment of this invention is realized when Z represents N, the bond between Y and Z is a single bond and X-Y respectively represents: $CR_1$=N; $CR_1$=$CR_5$; $CR_5$=$CR_1$; N=$CR_1$, and all other variables are as originally described.

Another embodiment of this invention is realized when Z represents C, X is O or S; Y represents $CR_1$ and the bond between Y and Z is a double bond as represent by the dotted line ---, and all other variables are as originally described.

Another embodiment of this invention is realized when $R_1$ represents:

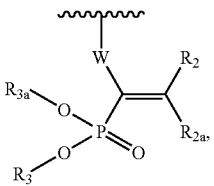

and all other variables are as originally described.

Another embodiment of this invention is realized when $R_1$ represents

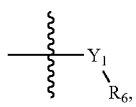

and all other variables are as originally described. A subembodiment of this invention is realized when $Y_1$ is —CO($CH_2$)$_n$ or —($CH_2$)$_n$.

Another embodiment of this invention is realized when $Y_1$ represents —($CH_2$)$_n$—, or —CO($CH_2$)$_n$—.

Another embodiment of this invention is realized when G represents N and all other variables are as originally described. Still another emobodiment of this invention is realized when G represents, Cry and all other variables are as originally described. Yet another emobodiment of this invention is realized when G represents, O and all other variables are as originally described.

Another embodiment of this invention is realized when M, M1 and M2 are CH, Z is N, G is N or CRy, Q is

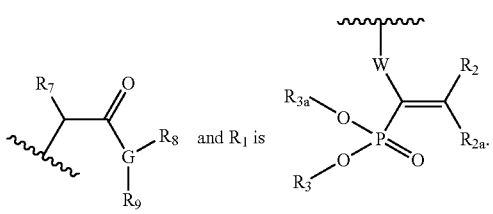

Another embodiment of the instant invention is realized when $R^a$ is selected from F, Cl, Br, I, OH, $CF_3$, N(R)$_2$, $NO_2$, CN, —$CONHR_8$, —CON($R_8$)$_2$, —O($CH_2$)$_n$COOR, —NH($CH_2$)$_n$OR, —COOR, —$OCF_3$, —NHCOR, —$SO_2$R, —$SO_2NR_2$, —SR, ($C_1$-$C_6$ alkyl)O—, —($CH_2$)$_n$—O—($CH_2$)$_m$ OR, —($CH_2$)$_n$$C_{1-6}$ alkoxy, (aryl)O—, —($CH_2$)$_n$OH, ($C_1$-$C_6$ alkyl)S(O)$_m$—, $H_2$N—C(NH)—, ($C_1$-$C_6$ alkyl)C(O)—, —($CH_2$)$_n$PO(OR)$_2$, —($CH_2$)$_n$OPO(OR)$_2$, $C_{2-6}$ alkenyl, and $C_1$-$C_{10}$ alkyl, said alkyl and alkenyl, optionally substituted with 1-3 groups selected from $C_1$-$C_6$ alkyl, and COOR;

Examples of compounds of formula I of this invention are:

1-[1-(3,3-Dimethyl-2-oxobutyl)-6-methoxy-1H-indazol-3-yl]-2-methylprop-1-en-1-yl dimethyl phosphate;

1-[1-(3,3-Dimethyl-2-oxobutyl)-6-methoxy-1H-indazol-3-yl]-2-methylprop-1-en-1-yl dihydrogen phosphate;

1-(1-{2-[(3,3-Dimethylbutyl)(ethyl)amino]-2-oxoethyl}-6-methoxy-1H-indazol-3-yl)-2-methylprop-1-en-1-yl dihydrogen phosphate;

1-[1-(3,3-Dimethyl-2-oxopentyl)-6-methoxy-1H-indazol-3-yl]-2-methylprop-1-en-1-yl dihydrogen phosphate;

1-[1-(3,3-Dimethyl-2-oxopentyl)-6-methoxy-1H-indazol-3-yl]-2-methylprop-1-en-1-yl methyl hydrogen phosphate;

Cyclopentylidene[1-(3,3-dimethyl-2-oxobutyl)-6-methoxy-1H-indazol-3-yl]methyl dihydrogen phosphate;

Cyclopentylidene[1-(3,3-dimethyl-2-oxopentyl)-6-methoxy-1H-indazol-3-yl]methyl dihydrogen phosphate;

N,N-Dibutyl-2-(3-isobutyryl-6-methoxy-1H-indazol-1-yl)acetamide;

N,N-Diisobutyl-2-(3-isobutyryl-6-methoxy-1H-indazol-1-yl)acetamide;

N-(Cyclopropylmethyl)-2-(3-isobutyryl-6-methoxy-1H-indazol-1-yl)-N-propylacetamide;

N-Cyclohexyl-N-ethyl-2-(3-isobutyryl-6-methoxy-1H-indazol-1-yl)acetamide;

2-(3-Isobutyryl-6-methoxy-1H-indazol-1-yl)-N,N-dipropylacetamide;

N-Butyl-N-ethyl-2-(3-isobutyryl-6-methoxy-1H-indazol-1-yl)acetamide,

N-Ethyl-2-(3-isobutyryl-6-methoxy-1H-indazol-1-yl)-N-(3-methylbutyl)acetamide;

N-Butyl-2-(3-isobutyryl-6-methoxy-1H-indazol-1-yl)-N-propylacetamide;

2-(3-Isobutyryl-6-methoxy-1H-indazol-1-yl)-N,N-bis(3-methylbutyl)acetamide;

1-(6-Methoxy-1-{2-[trans-octahydroisoquinolin-2(1H)-yl]-2-oxoethyl}-1H-indazol-3-yl)-2-methylpropan-1-one;

1-(6-Methoxy-1-{2-[cis-octahydroisoquinolin-2(1H)-yl]-2-oxoethyl}1-H-indazol-3-yl)-2-methylpropan-1-one;

N-(3,3-Dimethylbutyl)-2-(3-isobutyryl-6-methoxy-1H-indazol-1-yl)-N-propylacetamide;

(Z)-1-tert-Butyl-2-{6-methoxy-3-[2-methyl-1-(phosphonooxy)prop-1-en-1-yl]-1H-indazol-1-yl}vinyl dihydrogen phosphate; or (Z)-1-tert-Butyl-2-(3-isobutyryl-6-methoxy-1H-indazol-1-yl)vinyldihydrogen phosphate;

or a pharmaceutically acceptable salt, in vivo hydrolysable ester, enantiomer, diastereomer or mixture thereof.

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190)

When any variable (e.g. aryl, heterocycle, $R^1$, $R^6$ etc.) occurs more than one time in any constituent, its definition on each occurrence is independent at every other occurrence. Also, combinations of substituents/or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

Cycloalkyl is a specie of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkenyl is $C_2$-$C_6$ alkenyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Examples of aryl groups are phenyl, naphthyl, tetrahydronaphthyl, indanyl, biphenyl, phenanthryl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 3- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, dihydropyrrolyl, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from 2-azepinonyl, benzimidazolyl, 2-diazapinonyl, dihydroimidazolyl, dihydropyrrolyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl. Additional nitrogen atoms may be present together with the first nitrogen and oxygen or sulfur, giving, e.g., thiadiazole.

This invention is also concerned with compositions and methods of treating ocular hypertension or glaucoma by administering to a patient in need thereof one of the compounds of formula I alone or in combination with one or more of the following active ingredients, in combination with a β-adrenergic blocking agent such as timolol, betaxolol, levobetaxolol, carteolol, levobunolol, a parasympathomimetic agent such as epinephrine, iopidine, brimonidine, clonidine, para-aminoclonidine, carbonic anhydrase inhibitor such as dorzolamide, acetazolamide, metazolamide or brinzolamide, an EP4 agonist (such as those disclosed in WO 02/24647, WO 02/42268, EP 1114816, WO 01/46140, PCT Appln. No. CA2004000471, and WO 01/72268), a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine or a mixture thereof. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2\alpha}$ 1-$OCH_3$), or a hydroxy group ($PGF_{2\alpha}$ 1-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, smooth muscle and epithelial tissues and which are gated by membrane potential and intracellular $Ca^{2+}$.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration.

It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

A number of marketed drugs function as potassium channel antagonists. The most important of these include the compounds Glyburide, Glipizide and Tolbutamide. These potassium channel antagonists are useful as antidiabetic agents. The compounds of this invention may be combined with one or more of these compounds to treat diabetes.

Potassium channel antagonists are also utilized as Class 3 antiarrhythmic agents and to treat acute infarctions in humans. A number of naturally occurring toxins are known to block potassium channels including Apamin, Iberiotoxin, Charybdotoxin, Noxiustoxin, Kaliotoxin, Dendrotoxin(s), mast cell degranuating (MCD) peptide, and P-Bungarotoxin (D-BTX). The compounds of this invention may be combined with one or more of these compounds to treat arrhythmias.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Three classes of drugs are being investigated for the treatment of Alzheimer's disease cholinergic potentiators such as the anticholinesterase drugs (e.g., physostigmine (eserine), and Tacrine (tetrahydroaminocridine)); nootropics that affect neuron metabolism with little effect elsewhere (e.g., Piracetam, Oxiracetam; and those drugs that affect brain vasculature such as a mixture of ergoloid mesylates amd calcium channel blocking drugs including Nimodipine. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Anxiolytics, which are mild tranquilizers, are less effective than neuroleptics The present invention is related to novel compounds which are useful as potassium channel antagonists.

The compounds of this invention may be combined with anticholinesterase drugs such as physostigmine (eserine) and Tacrine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamin, Iberiotoxin, Charybdotoxin, Noxiustoxin, Kaliotoxin, Dendrotoxin(s), mast cell degranuating (MCD) peptide, β-Bungarotoxin (β-BTX) or a combination thereof in treating arrythmias. The compounds of this invention may further be combined with Glyburide, Glipizide, Tolbutamide or a combination thereof to treat diabetes.

The herein examples illustrate but do not limit the claimed invention. Each of the claimed compounds are potassium channel antagonists and are thus useful in the described neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamnic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The maxi-K channel blockers used can be administered in a therapeutically effective amount intravaneously, subcutaneously, topically, transdermally, parenterally or any other method known to those skilled in the art.

Ophthalmic pharmaceutical compositions are preferably adapted for topical administration to the eye in the form of solutions, suspensions, ointments, creams or as a solid insert. Ophthalmic formulations of this compound may contain from 0.01 ppm to 5% and especially 0.1 ppm to 1% of medicament. Higher dosages as, for example, about 10% or lower dosages can be employed provided the dose is effective in reducing intraocular pressure, treating glaucoma, increasing blood flow velocity or oxygen tension. For a single dose, from between 1 ng to 5000 μg, preferably 10 μg to 500 μg, and especially 100 ng to 200 μg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mamalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples given by way of illustration is demonstrative of the present invention. Definitions of the terms used in the examples are as follows:
SM—Starting material,
DMSO—dimethyl sulfoxide,
TLC—thin layer chromatography,
SGC—silica gel chromatography,
PhMgBr—phenylmagnesiumbromide
h=hr=hour,
THF—tetrahydrofuran,
DMF—dimethylformamide,
min—minute, LC/MS—liquid chromatography/mass spectrometry,
HPLC—high performance liquid chromatography,
PyBOP—Benzotriazol-1-yloxytris-(dimethylamino)phosphonium hexafluorophosphate, equiv=eq=equivalent,
NBS—N-Bromosuccinamide and
AIBN—2,2'-azobisisobutyronitrile.

The following examples given by way of illustration is demonstrative of the present invention. The compounds of this invention can be made, with modification where appropriate, in accordance with the Schemes below.

One method for the preparation of the compounds for this invention is illustrated in Scheme 1. α-Bromoketones can be prepared from ketones using the method of Cava et al. (J. Org. Chem. 1986, 51, 2044). Perkow reaction (see review by Lichtenthaler Chem. Rev. 61, 607, 1961) of the bromoketone with trimethyl phosphite provided the dimethyl enol phosphates. The heterocycle can be alkylated by electrophiles such as α-bromoketones to install the "head" group. The resulting dimethyl enol phosphates can be converted to dihydrogen enol phosphate using a modified method of T. Hata, et al. (Synthesis 1979, 189). While Hata et al. ran the reaction with neat trimethylsilyl bromide, use of a solvent such as dichoromethane or aeetonitrile is also useful.

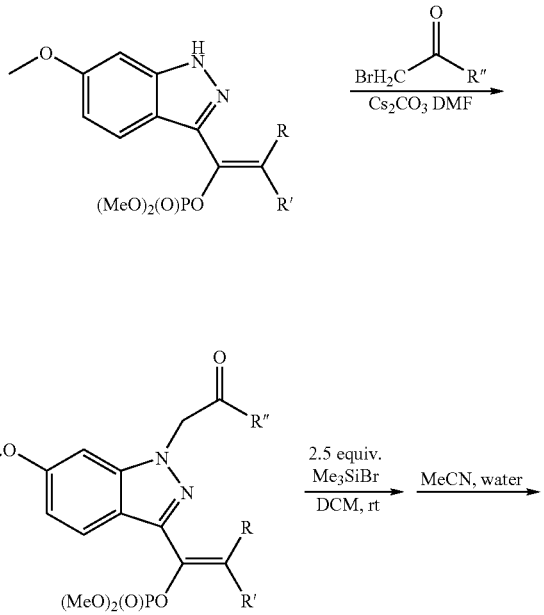

-continued

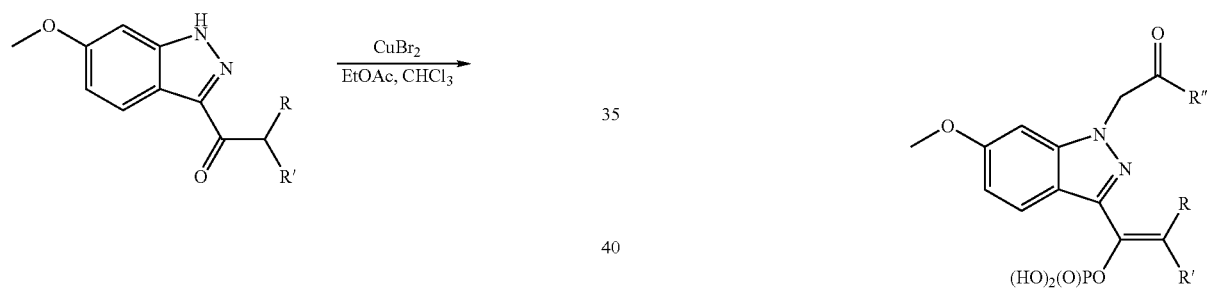

An alternative method is to start with a compound with the head group already installed. In effect the active Maxi-K ion channel blockers are converted into their pro-drugs in the form of enol phosphates. This approach is illustrated in Scheme 2. In some cases, a mixture of bromides were obtained. In favorable cases, these bromides can be separated and converted into respective enol phosphates individually.

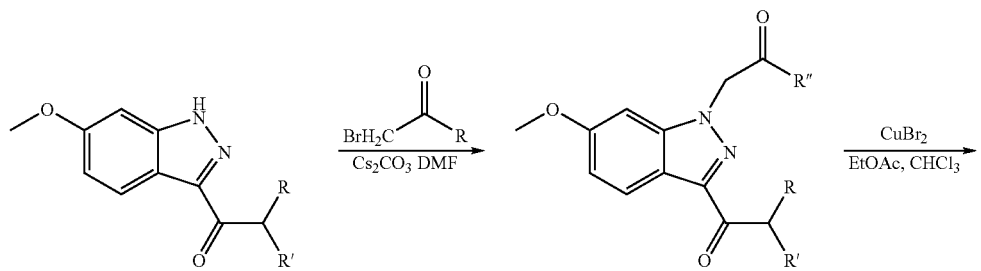

-continued

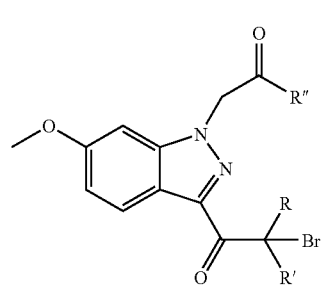 + 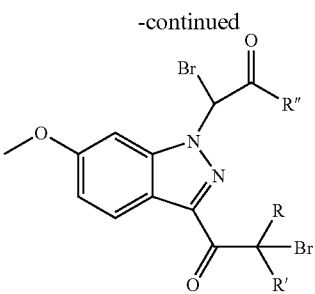 + 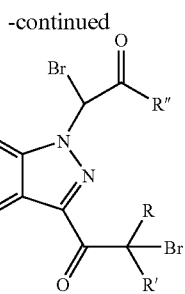

| excess P(OMe)₃ heat | excess P(OMe)₃ heat | excess P(OMe)₃ heat |

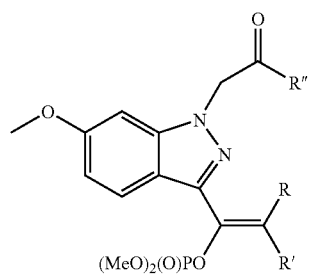 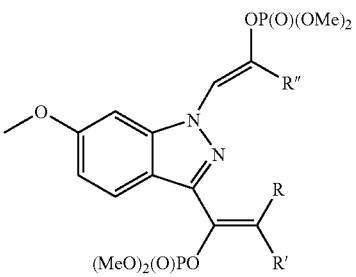 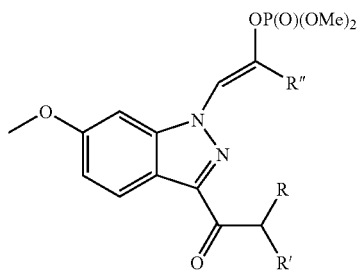

| 1) 2.5 equiv. Me₃SiBr DCM, rt  2) MeCN, water | 1) 2.5 equiv. Me₃SiBr DCM, rt  2) MeCN, water | 1) 2.5 equiv. Me₃SiBr DCM, rt  2) MeCN, water |

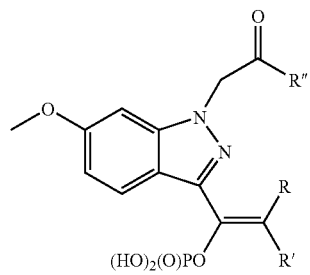 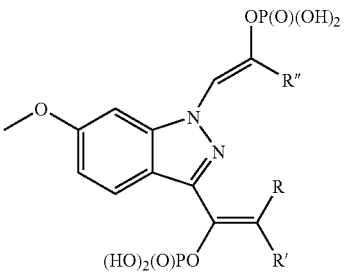 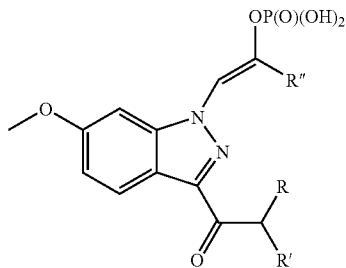

PREPARATIVE EXAMPLE 1

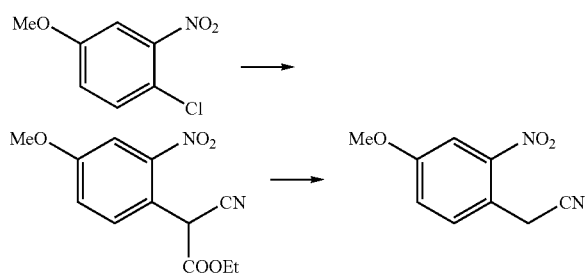

In a 500 mL flask was charged 336 mmoles (13.44 g; 60%) of NaH. Under argon 150 mL of DMSO was added, followed by dropwise addition of 32 mL of ethyl cyanoacetate (2.2 equiv.; 352 mmloes) at 5° C. After all the addition the reaction was warmed up to room temperature over 1 h. 30 g of starting nitro benzene derivative was added (160 mmoles) as a powder. The reaction mixture was heated in a closed system at 90° C. for 8 hours. Acidification and standard work-up gave a crude oily residue which was purified over a silica-gel column to give 39 g of desired crystalline product which was decarboxylated to give the benzyl nitrile as follows. Thirty eight grams of SM obtained above was dissolved in 400 mL of 1N sodium carbonate. The homogenous solution was stirred at rt for two days. TLC analysis indicated completion of reaction. The reaction mixture was acidified and extracted with ethyl acetate (100 mL×4). The combined organic phases was dried over sodium sulphate and concentrated and residue was subjected to SGC to give the desired product. $^1$H NMR CDCl$_3$: 7.72 (1H, d, J=3 Hz); 7.61 (1H, d, J=8.5 Hz); 7.25 (1H, dd, J=3 and 8.5 Hz); 4.17 (2H, s); 3.94 (3H, s). LC-MS [M+H]= 193.

PREPARATIVE EXAMPLE 2

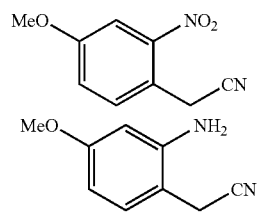

10 g of the benzylnitrile derivative was dissolved in 20 mL THF followed by dilution with 50 mL of methanol. The reaction mixture was taken in a pressure tube, Pd—C (10% wt/10 mole %) was added and the reaction mixture was hydrogenated at 40 psi. After the requisite amount of hydrogen for the reduction of the NO$_2$ group was consumed the reaction was stopped. TLC analysis indicated a spot to spot conversion. The reaction mixture was filtered over a pad of Celite and the filtrate was concentrated to a solid and used in the next step directly. Crude aniline derivative (52 mmoles was dissloved/suspended in 2N HCl (150 mL), cooled to 5° C. followed by the addition of 5.4 g of sodium nitrite in 10 mL of water. The reaction mixture was allowed to stir for 1 h with gradual warming to room temperature. TLC analysis indicated complete consumption of SM and the formation of a new spot. The reaction mixture was extracted with ethyl acetate (100 mL×4); organic phase was collected, dried and concentrated. The residue was purified by SGC to give desired product.

LCMS [M+H]=174

PREPARATIVE EXAMPLE 3

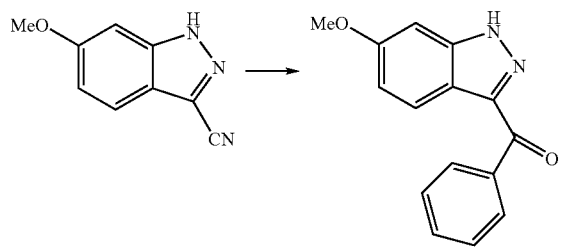

Nitrile (1.5 g) obtained from Preparative Example 2 was dissolved in 20 mL of dry THF and under argon and 3 equiv. of PhMgBr (1M in THF) was added at 5° C. The reaction mixture was stirred at room temperature for 1 h. The reaction was carefully quenched by addition of water and 1N HCl (15 mL). The quenched reaction mixture was stirred at room temperature for 1 hour then extracted with ethyl acetate (20 mL×3); combined organic phases were dried over sodium sulfate and concentrated to a solid residue which was azeotroped with toluene three times. LCMS [M+H]=253

PREPARATIVE EXAMPLE 4

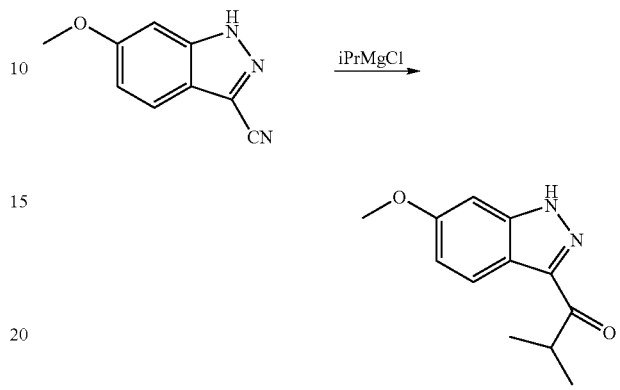

Weighed out 4.15 g of indazole and azeoptroped water with 2 toluene (100 ml) washings, pulling off toluene azeotrope by rotovap. Dried thoroughly under high vaccuum and performed argon purges. Dissolved in 40 ml dry THF and 92 ml dry ether under argon. Cooled to 5° C. in ice water bath. Charged 3 eq of isopropylmagnesium chloride (6 ml of a 2M solution in THF) and stirred for 0.5 hr at room temp. Carefully charged 1N HCl (240 ml) and stirred for 1 h. Monitored reaction by TLC. Extracted with EtOAc, rotovaped and produced desired product.

LCMS [M+H]=219

PREPARATIVE EXAMPLE 5

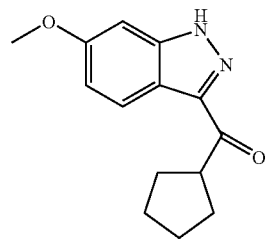

To a solution of intermediate from preparative Example 2 (1.00 g, 5.75 mmol) dissolved in THF (15 mL) was added cyclopentyl magnesium bromide (6.32 mL, 12.65 mmol) at 0° C. The reaction was allowed to warm to ambient temperature and was quenched with saturated NH$_4$Cl upon completion. The resulting reaction mixture was extracted with EtOAc and the combined organic layers were washed with brine, dried over MgSO$_4$, and concentrated in vacuo. The product was purified via SiO$_2$ gel chromatography to yield 580 mg of the desired product. $^1$H NMR (CDCl$_3$) δ: 1.702 (2

H, m), 1.803 (2 H, m), 2.005 (4 H, m), 3.904 (3 H, s), 4.070 (1 H, m), 6.915 (1 H, s), 7.010 (1 H, d), 8.272 (1 H, d).

PREPARATIVE EXAMPLE 6

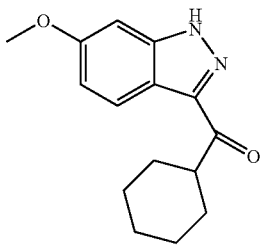

The desired compound was prepared by a procedure similar to the one described for Preparative Example 7, but cyclohexyl magnesium bromide was used in place of cyclopentyl magnesium bromide. $^1$H NMR (CDCl$_3$) δ: 1.327 (1 H, m), 1.479 (2 H, m), 1.604 (2 H, m), 1.781 (1 H, m), 1.861 (2 H, m), 2.000 (2 H, m), 3.641 (1 H, m), 3.902 (3 H, s), 6.923 (1 H, s), 7.008 (1 H, d), 8.259 (1 H, d).

Example 1

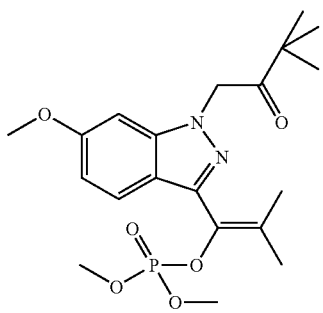

1-[1-(3,3-Dimethyl-2-oxobutyl)-6-methoxy-1H-indazol-3-yl]-2-methylprop-1-en-1-yl dimethyl phosphate Method I.

Step A. 2-Bromo-1-(6-methoxy-1H-indazol-3-yl)-2-methylpropan-1-one

The title compound was prepared from 1-(6-methoxy-1H-indazol-3-yl)-2-methylpropan-1-one and CuBr$_2$ using the method of Cava et al. (J. Org. Chem. 1986, 51, 2044). $^1$H NMR (CDCl$_3$, 500 MHz) δ 10.42 (br s, 1NH), 8.26 (d, 8.9 Hz, 1H), 7.03 (dd, 2.1 Hz, 1H), 6.94 (d, 2.1 Hz, 1H), 3.91 (s, 3H), 2.28 (s, 6H). LC-MS: 3.38 min. (m/Z=217.1, 297/299.0). It contained about 5% of a dibromide and was used without purification in the next step.

Step B: 1-(6-Methoxy-1H-indazol-3-yl)-2-methylprop-1-en-1-yl dimethyl phosphate

The title compound was prepared from 2-bromo-1-(6-methoxy-1H-indazol-3-yl)-2-methylpropan-1-one from the above by heating in excess trimethyl phosphite at 62° C. for 21 hours. Excess trimethyl phosphite was removed by vacuum distillation. The residue was purified on RP-HPLC using 10-90% MeCN gradient in water without TFA. Fractions containing the title compound were pooled, evaporated to dry, and recrystallized from ethyl acetate to give the title compound as colorless crystals. $^1$H NMR (CDCl$_3$, 500 MHz) δ 11.41 (br s, 1NH), 7.63 (d, 9.0 Hz, 1H), 6.815 (dd, 2.2 & 8.8 Hz, 1H), 6.77 (d, 1.8 Hz, 1H), 3.83 (s, 3H), 3.65 (d, $J_{P-H}$=11.2 Hz, 6H), 2.04 (d, $J_{P-H}$=2.5 Hz, 3H), 1.81 (d, $J_{P-H}$=3.5 Hz, 3H). LC-MS: 2.79 min. (m/Z=201.1, 327.0, 349.2).

Step C: 1-[1-(3,3-Dimethyl-2-oxobutyl)-6-methoxy-1H-indazol-3-yl]-2-methylprop-1-en-1-yl dimethyl phosphate Dissolve 0.52 g 1-(6-methoxy-1H-indazol-3-yl)-2-methylprop-1-en-1-yl dimethyl phosphate from the Step B above in 10 mL dry DMF. Weigh in 0.626 g cesium carbonate. Add 0.315 g (0.237 mL) 1-bromo-3,3-dimethylbutan-2-one and stir the resulting mixture at room temperature for 2 hours and at 50° C. for one day. Remove half of the DMF under reduced pressure. Dilute the residue with 1:1 MeCN and water, and purify on RP-HPLC using 20-100% MeCN gradient without TFA to give the title compound as a colorless solid. The title compound recrystallizes from 1:1 EtOAc and hexanes. $^1$H NMR (CDCl$_3$, 500 MHz) δ 7.70 (d, 9.0 Hz, 1H), 6.86 (dd, 2.0 & 8.7 Hz, 1H), 6.48 (d, 2.1 Hz, 1H), 5.33 (s, 2H), 3.87 (s, 3H), 3.57 (d, $J_{P-H}$=11.4 Hz, 6H), 2.02 (d, $J_{P-H}$=2.5 Hz, 3H), 1.83 (d, $J_{P-H}$=3.4 Hz, 3H), 1.32 (s, 9H).
$^{13}$C NMR (CDCl$_3$, 125 MHz) δ: 207.86, 159.95, 142.23, 140.48, 133.69 (d, $J_{P-C}$=9.6 Hz), 126.04 (d, $J_{P-C}$=7.7 Hz), 122.84, 118.38, 113.11, 90.32, 55.70, 54.69 (d, $J_{P-C}$=5.7 Hz), 53.46, 43.71, 26.55, 20.08, 18.69. LC-MS: 3.29 min. (m/Z=299.1, 447.0, 425.0).

Method II.

Step A. 1-(3-isobutyryl-6-methoxy-1H-indazol-1-yl)-3,3-dimethylbutan-2-one

Reaction of 1-(6-methoxy-1H-indazol-3-yl)-2-methylpropan-1-one with 1-bromo-3,3-dimethylbutan-2-one using a procedure similar to that described in Example 3 Step A gave the title compound. Recrystallization from 2:1 hexanes and EtOAc gave fine needles. $^1$H NMR (CDCl$_3$, 500 MHz) δ 8.25 (d, 8.9 Hz, 1H), 6.98 (dd, 2.0 & 8.9 Hz, 1H), 6.52 (d, 1.8 Hz, 1H), 5.37 (s, 2H), 3.87 (s, 3H), 3.86 (heptet, 6.9 Hz, 1H), 1.36 (s, 9H), 1.27 (d, 6.8 Hz, 6H). LC-MS: 3.70 min. (m/Z=317.1, 339.1).

Step B. 1-[3-(2-Bromo-2-methylpropanoyl)-6-methoxy-1H-indazol-1-yl]-3,3-dimethylbutan-2-one Reaction of 1-(3-isobutyryl-6-methoxy-1H-indazol-1-yl)-3,3-dimethylbutan-2-one with CuBr$_2$ using the procedure described in Method I Step A gave the title compound as the major product. It was obtained from RP-HPLC separation of the reaction mixture using 60-100% MeCN gradient without TFA. $^1$H NMR (CDCl$_3$, 500 MHz) δ 8.25 (d, 9.0 Hz, 1H), 7.01 (dd, 2.1 & 9.0 Hz, 1H), 6.57 (d, 2.1 Hz, 1H), 5.38 (s, 2H), 3.89 (s, 3H), 2.26 (s, 6H), 1.36 (s, 9H). LC-MS: 3.89 min. (m/Z=395/396.9, 417/418.9).

Step C: 1-[1-(3,3-Dimethyl-2-oxobutyl)-6-methoxy-1H-indazol-3-yl]-2-methylprop-1-en-1-yl dimethyl phosphate Reaction of 1-[3-(2-bromo-2-methylpropanoyl)-6-methoxy-1H-indazol-1-yl]-3,3-dimethylbutan-2-one from the above with trimethyl phosphite using the procedure as described in Method I Step B above provided the title compound identical to the one obtained with Method I.

Example 2

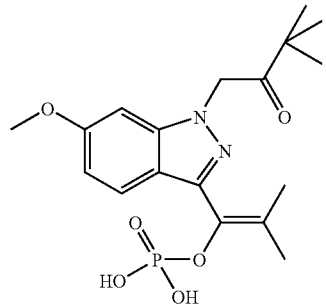

1-[1-(3,3-Dimethyl-2-oxobutyl)-6-methoxy-1H-indazol-3-yl]-2-methylprop-1-en-1-yl dihydrogen phosphate Dissolve 120 mg 1-[1-(3,3-dimethyl-2-oxobutyl)-6-methoxy-1H-indazol-3-yl]-2-methylprop-1-en-1-yl dimethyl phosphate from Example 1 in 0.75 mL anhydrous DCM. Cool the solution in an ice bath under nitrogen. Add 108 mg trimethylsilyl bromide and let the reaction mixture sit at room temperature for 2.5 hours. Remove solvent under reduced pressure. The residue was dissolved in a mixture of MeCN and water and purified by RP-HPLC using 10-100% MeCN gradient with about 0.05% TFA to give the title compound as a colorless solid after lyophilization. This reaction can also be carried out in MeCN. The title compound can also be purified by recrystallization in anhydrous MeCN.

$^1$H NMR (CDCl$_3$, 500 MHz) δ 7.61 (d, 8.9 Hz, 1H), 6.87 (dd, 2.1 & 8.9 Hz, 1H), 6.78 (d, 1.8 Hz, 1H), 6.25 (v br s, ~3H), 5.32 (s, 2H), 3.87 (s, 3H), 1.95 (d, $J_{P-H}$=2.5 Hz, 3H, overlap with solvent residual peak), 1.81 (d, $J_{P-H}$=3.4 Hz, 3H), 1.26 (s, 9H). LC-MS: 2.73 min. (m/Z=299.1, 397.0, 419.0).

Example 3

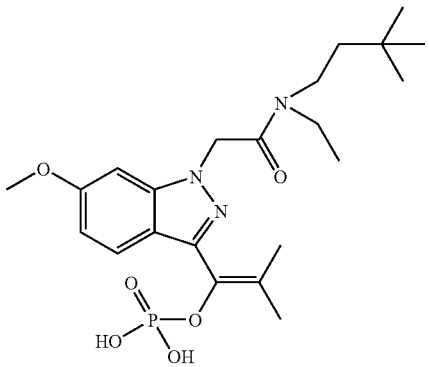

1-(1-{2-[(3,3-Dimethylbutyl)(ethyl)amino]-2-oxoethyl}-6-methoxy-1H-indazol-3-yl)-2-methylprop-1-en-1-yl dihydrogen phosphate Step A: Ethyl (3-isobutyryl-6-methoxy-1H-indazol-1-yl)acetate Dissolve 5.456 g of 1-(6-methoxy-1H-indazol-3-yl)-2-methylpropan-1-one in 100 mL anhydrous DMF. Weigh in 8.96 g cesium carbonate followed by 4.593 g ethyl bromoacetate. The resulting mixture was stirred at room temperature overnight. The solvent was removed under reduced pressure. Partition the residue between EtOAc and water. Extract the aqueous layer with EtOAc several times. The combined organic extract was washed with water (3×) and saturated brine, dried over anhydrous Na$_2$SO$_4$, and evaporated to give the crude product. The title compound was obtained by recrystallization from 40 mL 4:1 hexanes and EtOAc. $^1$H NMR (CDCl$_3$, 500 MHz) δ 8.26 (d, 8.9 Hz, 1H), 7.00 (dd, 2.1 & 9.0 Hz, 1H), 6.685 (d, 2.1 Hz, 1H), 5.17 (s, 2H), 4.28 (q, 7.1 Hz, 2H), 3.90 (s, 3H), 3.87 (heptet, 6.9 Hz, 1H), 1.29 (t, 7.1 Hz, 3H), 1.28 (d, 6.8 Hz, 6H). LC-MS: 3.51 min. (m/Z=305.1, 327.0).

Step B: (3-Isobutyryl-6-methoxy-1H-indazol-1-yl)acetic acid

Dissolve 1.68 g ethyl (3-isobutyryl-6-methoxy-1H-indazol-1-yl)acetate in 50 mL MeOH at 45° C. Add 10 mL water and 1.5 mL 5 N NaOH solution. The resulting mixture was heated overnight and evaporated to dry. The residue was taken up in water, acidified with 0.8 mL concentrated HCl, and extracted with 3×50 mL EtOAc. The combined organic extract was washed with water and saturated brine, dried over anhydrous Na$_2$SO$_4$, and evaporated to give the title compound as a white solid. $^1$H NMR (CDCl$_3$, 500 MHz) δ 8.27 (d, 8.9 Hz, 1H), 7.01 (dd, 2.1 & 8.9 Hz, 1H), 6.69 (d, 2.1 Hz, 1H), 5.23 (s, 2H), 3.91 (s, 3H), 3.85 (heptet, 6.9 Hz, 1H), 1.28 (d, 7.1 Hz, 6H). In NOE difference spectrum, irradiation of the 5.23 ppm singlet showed positive NOE at the 6.69 ppm doublet. LC-MS: 2.94 min. (m/Z=277.0, 299.0).

Step C: N-Ethyl-3,3-dimethylbutan-1-amine hydrochloride

The title compound was prepared from commercially available ethylamine and 3,3-dimethylbutyraldehye using sodium triacetoxyborohydride (Abdel-Magid, et al. J. Org. Chem. 1996, 61, 3849). $^1$H NMR (CD$_3$OD, 500 MHz) δ 3.07 (q, 7.1 Hz, 2H), 2.97-3.02 (m, 2H), 1.57-1.62 (m, 2H), 1.32 (t, 7.2 Hz, 3H), 0.98 (s, 9H).

Step D: N-(3,3-Dimethylbutyl)-N-ethyl-2-(3-isobutyryl-6-methoxy-1H-indazol-1-yl)acetamide Charge a 13×100 mm screw-capped tube with 27.6 mg (3-isobutyryl-6-methoxy-1H-indazol-1-yl)acetic acid, 23.0 mg HOBt hydrate, 18.6 mg N-ethyl-3,3-dimethylbutan-1-amine hydrochloride, and 89 μL DIEA. Dissolve the mixture in 1 mL anhydrous DMF. Add 38.3 mg EDC HCl salt and let the mixture sit at room temperature overnight. The title compound was isolated from the reaction mixture using RP-HPLC with 65-100% MeCN gradient with 0.1% TFA. LC-MS: 3.89 min. (m/Z=388.2, 410.1)

Step E: 2-[3-(2-Bromo-2-methylpropanoyl)-6-methoxy-1H-indazol-1-yl]-N-(3,3-dimethylbutyl)-N-ethylacetamide Reaction of N-(3,3-dimethylbutyl)-N-ethyl-2-(3-isobutyryl-6-methoxy-1H-indazol-1-yl)acetamide with CuBr$_2$ using the procedure described in Method I Step A of Example 1 gave the title compound following RP-HPLC with 70-100% MeCN gradient without TFA. $^1$H NMR (CDCl$_3$, 500 MHz) showed two sets of signals for some resonances due to amide rotamers in about 1:1 ratio: δ 8.22 (d, 8.9 Hz, 1H), 7.00 (dd, 2.1 & 8.9 Hz, 1H), 6.98 & 6.91 (d, 2.1 Hz, 1H), 5.25 & 5.19 (s, 2H), 3.92 & 3.91 (s, 3H), 3.53~3.56 & 3.35~3.38 (m, 2H), 3.53 & 3.42 (q, 7.1 Hz, 2H), 2.26 (s, 6H), 1.60~1.64 & 1.43~1.47 (m, 2H), 1.04 & 0.93 (s, 9H). LC-MS: 4.20 min. (m/Z=466/468.1, 488/490.1)

Step F: 1-(1-{2-[(3,3-Dimethylbutyl)(ethyl)amino]-2-oxoethyl}-6-methoxy-1H-indazol-3-yl)-2-methylprop-1-en-1-yl dimethyl phosphate Reaction of 2-[3-(2-bromo-2-methylpropanoyl)-6-methoxy-1H-indazol-1-yl]-N-(3,3-dimethylbutyl)-N-ethylacetamide from the above with trimethyl phosphite using the procedure as described in Method I Step B Example 1 provided the title compound following RP-HPLC using 50-100% MeCN gradient without TFA. $^1$H NMR (CDCl$_3$, 500 MHz) showed two amide rotamers in about 1.3:1 ratio:o Major rotamer: 7.65 (d, 8.7 Hz, 1H), 6.83 (dd, 9.0 & 2.1 Hz, 1H), 6.805 (d, 1.9 Hz, 1H), 5.15 (s, 2H), 3.88 (s, 3H), 3.55 (d, 11.2 Hz, 6H), 3.48 (q, 7.1 Hz, 2H), 3.32~3.35 (m, 2H), 2.01 (d, 2.5 Hz, 3H), 1.83 (d, 3.5 Hz, 3H), 1.40~1.44 (m, 2H), 1.14 (t, 7.1 Hz, 3H), 0.91 (s, 9H). Minor rotamer: 7.66 (d, 8.7 Hz, 1H), 6.83 (dd, 9.0 & 2.1 Hz, 1H), 6.77 (d, 1.8 Hz, 1H), 5.12 (s, 2H), 3.88 (s, 3H), 3.54 (d, 11.4 HZ, 6H), 3.41~3.44 (m, 2H), 3.38 (q, 7.2 Hz, 2H), 2.01 (d, 2.5 Hz, 3H), 1.84 (d, 3.5 Hz, 3H), 1.56~1.60 (m, 2H), 1.12 (t, 7.1 Hz, 3H), 1.00 (s, 9H). $^{13}$C NMR (CDCl$_3$, 125 MHz): Major rotamer: 165.85, 160.95, 142.34, 140.22, 133.82 (d, J$_{C-P}$=9.6 Hz), 125.87 (d, J$_{C-P}$=6.7 Hz), 122.56, 118.22, 113.71, 90.89, 55.74, 54.685 (d, J$_{C-P}$=5.8 Hz), 51.96, 42.99, 42.51, 41.05, 29.99, 29.46, 20.13, 18.75, 14.51; Minor rotamer: 165.71, 159.96, 142.45, 140.22, 133.88 (d, J$_{C-P}$=9.6 Hz), 125.79 (d, J$_{C-P}$=7.7 Hz), 122.60, 118.27, 113.51, 90.94, 55.74, 54.685 (d, J$_{C-P}$=5.8 Hz), 51.18, 44.03, 42.82, 41.50, 29.96, 29.46, 20.18, 18.75, 13.21. LC-MS: 3.67 min. (m/Z=518.3, 496.3, 370.4).

Step G: 1-(1-{2-[(3,3-Dimethylbutyl)(ethyl)amino]-2-oxoethyl}-6-methoxy-1H-indazol-3-yl)-2-methylprop-1-en-1-yl dihydrogen phosphate Reaction of 1-(1-{2-[(3,3-dimethylbutyl)(ethyl)amino]-2-oxoethyl}-6-methoxy-1H-indazol-3-yl)-2-methylprop-1-en-1-yl dimethyl phosphate with trimethylsilyl bromide as described in Example 2 provided the title compound. It was isolated by RP-HPLC using 10-100% MeCN gradient without TFA as a colorless solid following lyophilization. $^1$H NMR (CD$_3$CN, 500 MHz) showed two amide rotamers in about 6:7 ratio: δ 7.55 (d, 8.7 Hz, 1H), 6.88 & 6.87 (d, 1.9 Hz, 1H), 6.84 (dd, 2.1 & 8.9 Hz, 1H), 5.23 & 5.21 (s, 2H), 3.88 & 3.87 (s, 3H), 3.31~3.48 (m, 4H, overlapping with residual water peak), 1.94 (d, 1.8 Hz, 3H), 1.81-1.82 (m, 3H), 1.61- 1.64 & 1.42~1.46 (m, 2H), 1.26 & 1.10 (t, 7.1 Hz, 3H), 0.99 & 0.91 (s, 9H). LC-MS: 3.18 min. (m/Z=370.2, 468.1).

Example 4

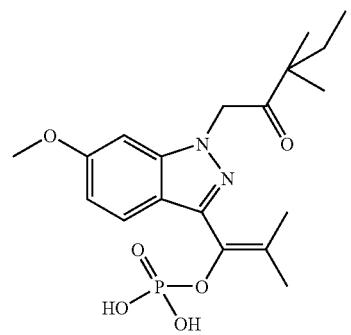

1-[1-(3,3-Dimethyl-2-oxopentyl)-6-methoxy-1H-indazol-3-yl]-2-methylprop-1-en-1-yl dihydrogen phosphate Step A. 1-Bromo-3,3-dimethylpentan-2-one The title compound was prepared from commercially available 3,3-dimethylpentan-2-one using the method of Gaudry and Marguet (Org. Syn. CV 6, 193) and isolated as a yellowish liquid. $^1$H NMR (CDCl$_3$, 500 MHz) δ 4.17 (s, 2H), 1.63 (q, 7.5 Hz, 2H), 1.21 (s, 6H), 0.85 (t, 7.5 Hz, 3H).

Step B. 1-[1-(3,3-Dimethyl-2-oxopentyl)-6-methoxy-1H-indazol-3-yl]-2-methylprop-1-en-1-yl dimethyl phosphate The title compound was prepared from 1-(6-methoxy-1H-indazol-3-yl)-2-methylprop-1-en-1-yl dimethyl phosphate from Method I Step B of Example 1 and 1-bromo-3,3-dimethylpentan-2-one from the above using a procedure similar to described in Method I Step C of Example 1. It was purified on RP-HPLC using 30-100% MeCN gradient without TFA to give colorless solid after lyophilization. $^1$H NMR (CDCl$_3$, 500 MHz) δ 7.70 (d, 9.0 Hz, 1H), 6.86 (dd, 2.1 & 8.9 Hz, 1H), 6.48 (d, 2.1 Hz, 1H), 5.29 (s, 2H), 3.86 (s, 3H), 3.56 (d, 11.3 Hz, 6H), 2.02 (d, 2.5 Hz, 3H), 1.82 (d, 3.5 Hz, 3H), 1.74 (q, 7.5 Hz, 2H), 1.28 (s, 6H), 0.94 (t, 7.6 Hz, 3H). NOE difference spectrum from irradiating 5.29 ppm singlet showed positive NOE at 6.48 ppm doublet and 1.28 ppm singlet. LC-MS: 3.48 min. (m/Z=313.2, 461.2, 439.2).

Step C. 1-[1-(3,3-Dimethyl-2-oxopentyl)-6-methoxy-1H-indazol-3-yl]-2-methylprop-1-en-1-yl dihydrogen phosphate The title compound was prepared from 1-[1-(3,3-dimethyl-2-oxopentyl)-6-methoxy-1H-indazol-3-yl]-2-methylprop-1-en-1-yl dimethyl phosphate using method described in Example 2. It was obtained as a colorless solid after RP-HPLC (10-100% MeCN gradient without TFA) and lyophilization.

$^1$H NMR (CDCl$_3$, 500 MHz) δ 7.605 (d, 9.1 Hz, 1H), 6.87 (dd, 1.8 & 9.0 Hz, 1H), 6.45 (1.9 Hz, 1H), 5.14 (s, 2H), 3.86 (s, 3H), 3.16 (v br s, OH+H$_2$O), 2.01 (br s, 3H), 1.82 (d, $J_{H-P}$=3.0 Hz, 3H), 1.70 (q, 7.5 Hz, 2H), 1.24 (s, 6H), 0.91 (t, 7.5 Hz, 3H). LC-MS: 2.89 min. (m/Z=313.2, 411.1).

Example 5

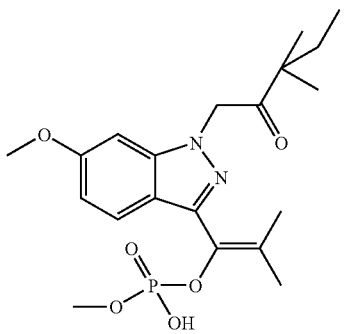

1-[1-(3,3-Dimethyl-2-oxopentyl)-6-methoxy-1H-indazol-3-yl]-2-methylprop-1-en-1-yl methyl hydrogen phosphate If the reaction in Step C of Example 4 was not carried out to completion, a mixture of 1-[1-(3,3-dimethyl-2-oxopentyl)-6-methoxy-1H-indazol-3-yl]-2-methylprop-1-en-1-yl methyl hydrogen phosphate and 1-[1-(3,3-dimethyl-2-oxopentyl)-6-methoxy-1H-indazol-3-yl]-2-methylprop-1-en-1-yl dihydrogen phosphate was obtained. This mixture was separated by RP-HPLC using a Zorbax SB-C18 column with a 10-90% MeCN gradient having 0.1% TFA. The title compound eluted slower than 1-[1-(3,3-dimethyl-2-oxopentyl)-6-methoxy-1H-indazol-3-yl]-2-methylprop-1-en-1-yl dihydrogen phosphat on this column. It was obtained as a colorless solid after lyophilization. $^1$H NMR (DMSO-$d_6$, 500 MHz) δ 7.55 (d, 9.0 Hz, 1H), 6.92 (d, 2.1 Hz, 1H), 6.76 (dd, 2.0 & 8.9 Hz, 1H), 5.50 (s, 2H), 3.78 (s, 3H), 3.27 (d, 11.5 Hz, 3H), 1.88 (d, 2.3 Hz, 3H), 1.75 (d, 3.7 Hz, 3H), 1.66 (q, 7.4 Hz, 2H), 1.19 (s, 6H), 0.81 (t, 7.5 Hz, 3H). LC-MS: 2.97 min. (m/Z=313.2, 425.1, 447.1).

Example 6

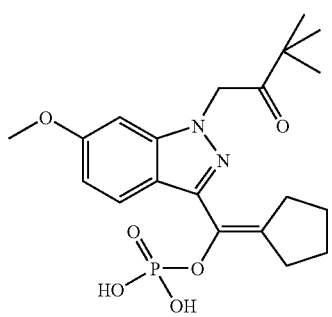

Cyclopentylidene[1-(3,3-dimethyl-2-oxobutyl)-6-methoxy-1H-indazol-3-yl]methyl dihydrogen phosphate Step A. (1-Bromocyclopentyl)(6-methoxy-1H-indazol-3-yl)methanone The title compound was prepared from cyclopentyl(6-methoxy-1H-indazol-3-yl)methanone and $CuBr_2$ using the procedure described in Method I Step A of Example 1 followed by RP-HPLC with 30-100% MeCN gradient without TFA. $^1$H NMR (CDCl$_3$, 500 MHz) δ 8.27 (d, 9.0 Hz, 1H), 7.03 (dd, 2.1 & 9.0 Hz, 1H), 6.94 (d, 1.8 Hz, 1H), 3.91 (s, 3H), 2.75~2.81 (m, 2H), 2.53~2.60 (m, 2H), 2.10~2.20 (m, 2H), 1.85~1.93 (m, 2H). LC-MS: 4.01 min. (m/Z=243.2, 175.1, 323/325.1).

Step B. Cyclopentylidene(6-methoxy-1H-indazol-3-yl)methyl dimethyl phosphate

The title compound was prepared from (1-bromocyclopentyl)(6-methoxy-1H-indazol-3-yl)methanone and trimethyl phosphite using the procedure described in Method I Step B of Example 1 followed by RP-HPLC purification using 20-100% MeCN gradient. It was isolated as a white solid following lyophilization. $^1$H NMR (CDCl$_3$, 500 MHz) δ 7.79 (d, 8.9 Hz, 1H), 6.85 (dd, 2.1 & 9.0 Hz, 1H), 6.81 (d, 1.8 Hz, 1H), 3.88 (s, 3H), 3.67 (d, 11.3 Hz, 6H), 2.72~2.79 (m, 2H), 2.53~2.59 (m, 2H), 1.70~1.81 (m, 4H). LC-MS: 3.00 min. (n/Z=227.2, 353.2, 375.2).

Step C. Cyclopentylidene[1-(3,3-dimethyl-2-oxobutyl)-6-methoxy-1H-indazol-3-yl]methyl dimethyl phosphate The title compound was prepared from cyclopentylidene (6-methoxy-1H-indazol-3-yl)methyl dimethyl phosphate and 1-bromo-3,3-dimethylbutan-2-one using the procedure described in Method I Step C of Example 1 followed by RP-HPLC purification using 30-100% MeCN gradient without TFA. It was obtained as a solid following lyophilization. LC-MS: 3.56 min. (m/Z=325.2, 451.2, 473.1).

Step D. Cyclopentylidene[1-(3,3-dimethyl-2-oxobutyl)-6-methoxy-1H-indazol-3-yl]methyl dihydrogen phosphate The title compound was prepared from cyclopentylidene [1-(3,3-dimethyl-2-oxobutyl)-6-methoxy-1H-indazol-3-yl] methyl dimethyl phosphate using the procedure described in Example 2. It was purified on RP-HPLC using 15-100% MeCN gradient with 0.1% TFA and obtained as a white solid after lyophilization. $^1$H NMR (CD$_3$CN, 500 MHz) δ 7.73 (d, 8.9 Hz, 1H), 6.82 (dd, 2.0 & 8.9 Hz, 1H), 7.73 (d, 1.8 Hz, 1H), 5.33 (s, 2H), 3.85 (s, 3H), 2.63~2.67 (m, 2H), 2.45~2.49 (m, 2H), 1.67~1.72 (m, 4H), 1.27 (s, 9H). LC-MS: 2.93 min. (m/Z=325.2, 423.2, 445.2).

Example 7

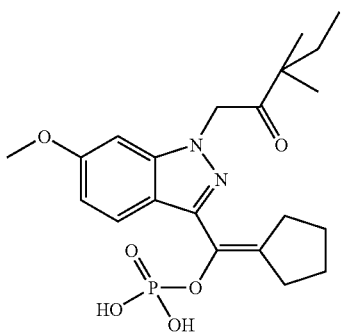

Cyclopentylidene[1-(3,3-dimethyl-2-oxopentyl)-6-methoxy-1H-indazol-3-yl]methyl dihydrogen phosphate Step A. Cyclopentylidene[1-(3,3-dimethyl-2-oxopentyl)-6-methoxy-1H-indazol-3-yl]methyl dimethyl phosphate The title compound was prepared from cyclopentylidene (6-methoxy-1H-indazol-3-yl)methyl dimethyl phosphate from Step B Example 6 and 1-Bromo-3,3-dimethylpentan-2-one from Step A Example 4 using the procedure described in Method I Step C of Example 1 followed by RP-HPLC purification using 35~100% MeCN gradient without TFA. It was obtained as a colorless solid after lyophilization. LC-MS: 3.70 min. (m/Z=339.2, 465.2, 487.1).

Step B. Cyclopentylidene[1-(3,3-dimethyl-2-oxopentyl)-6-methoxy-1H-indazol-3-yl]methyl dihydrogen phosphate The title compound was prepared from cyclopentylidene [1-(3,3-dimethyl-2-oxopentyl)-6-methoxy-1H-indazol-3-yl]methyl dimethyl phosphate using the procedure described in Example 2. It was purified on RP-HPLC using 20-100% MeCN gradient with 0.1% TFA and obtained as a white solid after lyophilization. $^1$H NMR (CD$_3$CN, 500 MHz) δ 7.74 (d, 8.9 Hz, 1H), 6.815 (dd, 2.1 & 8.9 Hz, 1H), 7.73 (d, 1.8 Hz, 1H), 5.28 (s, 2H), 3.84 (s, 3H), 2.62~2.67 (m, 2H), 2.45~2.49 (m, 2H), 1.66~1.72 (m, 6H), 1.23 (s, 6H), 0.88 (t, 7.4 Hz, 3H). LC-MS: 3.08 min. (m/Z=339.3, 437.2, 459.2).

Examples 8~19

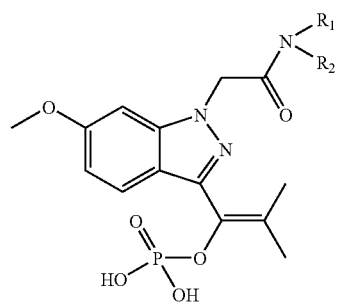

Step A. The following acetamide derivatives in Table 1 were prepared from (3-isobutyryl-6-methoxy-1H-indazol-1-yl)acetic acid and appropriate amines using the procedure described in Step D of Example 3. They were purified by RP-HPLC. They can also be purified by alternative means. For example, Compound 19A was recrystallized from 10:1 hexanes and EtOAc and its $^1$H NMR (CD$_3$OD, 500 MHz) showed two sets of signals for some resonances due to amide rotamers in about 1:1 ratio: δ 8.22 (d, 8.9 Hz, 1H), 6.98 (br d, 8.9 Hz, 1H), 6.89 and 6.82 (d, each 1.4 Hz, 1H), 5.22 and 5.20 (s, 2H), 3.90 (s, 3H), 3.88 (heptet, 6.7 Hz, 1H), 3.43~3.46 and 3.36~3.40 (m, 2H), 3.35~3.39 and 3.30~3.33 (m, 2H), 1.56~1.62 (m, 2H), 1.54~1.57 and 1.44~1.48 (m, 2H), 1.27 (d, 6.8 Hz, 6H), 1.02 and 0.93 (s, 9H), 0.99 and 0.87 (t, 7.3 Hz, 3H).

TABLE 1

Acetamide Derivatives as Precursors to Examples 8-19.

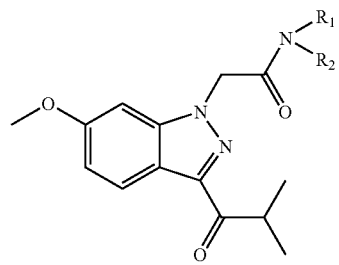

| Compound | R$_1$ | R$_2$ | t$_r$, min. | m/Z |
|---|---|---|---|---|
| 8A | n-Bu | n-Bu | 3.93 | 388.2, 410.1 |
| 9A | i-Bu | i-Bu | 3.90 | 388.2, 410.1 |
| 10A | cyclopropylmethyl | n-Pr | 3.67 | 372.1, 394.1 |
| 11A | cyclohexyl | Et | 3.80 | 386.2, 408.1 |
| 12A | n-Pr | n-Pr | 3.64 | 360.1, 382.1 |
| 13A | n-Bu | Et | 3.64 | 360.1, 382.1 |
| 14A | i-Amyl | Et | 3.78 | 374.2, 396.1 |
| 15A | n-Bu | n-Pr | 3.80 | 374.2, 396.1 |
| 16A | i-Amyl | i-Amyl | 4.20 | 416.2, 438.2 |
| 17A | Trans- (decalin) | | 3.87 | 398.1, 420.1 |
| 18A | Cis- (decalin) | | 3.80 | 398.1, 420.1 |
| 19A | 3,3-Dimethylbutyl | n-Pr | 4.03 | 402.2, 424.2 |

Steps B~D. The conversion of compounds 8A~19A into Examples 8-19 can be accomplished using procedures described in Example 3 Steps E-G.

Table 2. Examples 8-19

TABLE 2

Examples 8-19

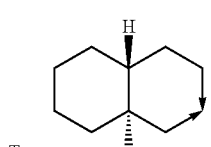

| Example | R₁ | R₂ |
| --- | --- | --- |
| 8 | n-Bu | n-Bu |
| 9 | i-Bu | i-Bu |
| 10 | cyclopropylmethyl | n-Pr |
| 11 | cyclohexyl | Et |
| 12 | n-Pr | n-Pr |
| 13 | n-Bu | Et |
| 14 | i-Amyl | Et |
| 15 | n-Bu | n-Pr |
| 16 | i-Amyl | i-Amyl |
| 17 | 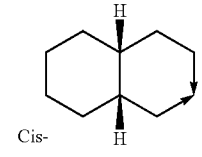 Trans- | |
| 18 | Cis- | |
| 19 | 3,3-Dimethylbutyl | n-Pr |

Example 20

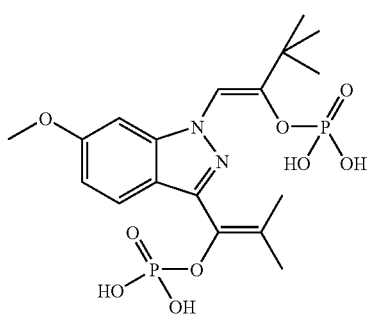

(Z)-1-tert-Butyl-2-{6-methoxy-3-[2-methyl-1-(phosphonooxy)prop-1-en-1-yl]-1H-indazol-1-yl}vinyl dihydrogen phosphate Step A. 1-Bromo-1-[3-(2-bromo-2-methylpropanoyl)-6-methoxy-1H-indazol-1-yl]-3,3-dimethylbutan-2-one Some of the title dibromide was obtained during the RP-HPLC purification in Method II Step B of Example 1. LC-MS: 4.18 min. (m/Z=393/394.9, 473/474.8/476.8).

Step B. (Z)-1-tert-Butyl-2-(3-{1-[(dimethoxyphosphoryl)oxy]-2-methylprop-1-en-1-yl}-6-methoxy-1H-indazol-1-yl)vinyl dimethyl phosphate The title compound was prepared from 1-bromo-1-[3-(2-bromo-2-methylpropanoyl)-6-methoxy-1H-indazol-1-yl]-3,3-dimethylbutan-2-one from Step A above and trimethyl phosphite using the method in Method I Step B of Example 1. It was purified by RP-HPLC using 10-80% MeCN gradient without TFA. ¹H NMR (CDCl₃, 500 MHz) δ 7.68 (d, 8.9 Hz, 1H), 6.865 (dd, 2.1 & 8.9 Hz, 1H), 6.71 (d, $J_{H-P}$=3.0 Hz, 1H), 6.67 (d, 2.0 Hz, 1H), 3.89 (s, 3M), 3.63 (d, $J_{H-P}$=11.2 Hz, 6H), 3.36 (d, $J_{H-P}$=11.6 Hz, 6H), 2.02 (d, $J_{H-P}$=2.5 Hz, 3H), 1.88 (d, $J_{H-P}$=3.4 Hz, 3H), 1.38 (s, 9H). LC-MS: 3.26 min. (m/Z=407.1, 533.0, 555.0). It was noted that a faster-eluting undesirable isomeric side-product was also obtained during this reaction.

Step C. (Z)-1-tert-Butyl-2-{6-methoxy-3-[2-methyl-1-(phosphonooxy)prop-1-en-1-yl]-1H-indazol-1-yl}vinyl dihydrogen phosphate The title compound was prepared from (Z)-1-tert-butyl-2-(3-{1-[(dimethoxyphosphoryl)oxy]-2-methylprop-1-en-1-yl}-6-methoxy-1H-indazol-1-yl)vinyl dimethyl phosphate from the Step B above using the procedure in Example 2. It was purified by RP-HPLC using 10~90% MeCN gradient with 0.06% TFA in the water to give a white solid after lyophilization. ¹H NMR (CD₃CN, 500 MHz) □7.47 (d, 8.7 Hz, 1H), 6.89 (d, 8.7 Hz, 1H), 6.86 (s, 1H), 6.76 (d, $J_{H-P}$=2.3 Hz, 1H), 3.89 (s, 3H), 1.95 (d, $J_{H-P}$=2.5 Hz, ~3H overlapping with solvent residual), 1.70 (d, $J_{H-P}$=2.3 Hz, 1H), 1.33 (s, 9H). LC-MS: 2.75 min. (m/Z=477.0, 379.1, 499).

Example 21

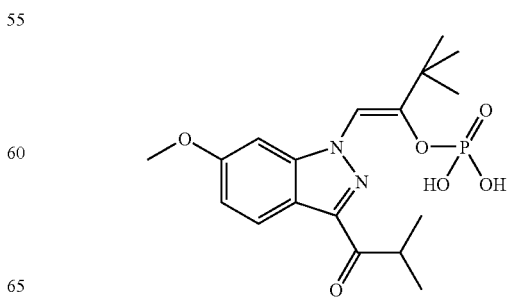

(Z)-1-tert-Butyl-2-(3-isobutyryl-6-methoxy-1H-indazol-1-yl)vinyl dihydrogen phosphate

Step A. 1-Bromo-1-(3-isobutyryl-6-methoxy-1H-indazol-1-yl)-3,3-dimethylbutan-2-one The title compound was obtained as a minor component during the RP-HPLC purification in Method II Step B of Example 1. LC-MS: 3.90 min. (m/Z=417/418.9, 395/397.0).

Step B. (Z)-1-tert-Butyl-2-(3-isobutyryl-6-methoxy-1H-indazol-1-yl)vinyl dimethyl phosphate The title compound was prepared from 1-bromo-1-(3-isobutyryl-6-methoxy-1H-indazol-1-yl)-3,3-dimethylbutan-2-one from Step A above using the procedure in Method I Step B of Example 1. It was purified by RP-HPLC using 10~100% MeCN gradient without TFA. LC-MS: 3.59 min. (m/Z=447.0, 425.0). It was noted that a faster-eluting undesirable isomeric side-product was also obtained during this reaction.

Step C. (Z)-1-tert-Butyl-2-(3-isobutyryl-6-methoxy-1H-indazol-1-yl)vinyl dihydrogen phosphate The title compound was prepared from (Z)-1-tert-butyl-2-(3-isobutyryl-6-methoxy-1H-indazol-1-yl)vinyl dimethyl phosphate from the Step B above using the procedure in Example 2. It was purified by RP-HPLC using 25~100% MeCN gradient with 0.06% TFA in the water to give a white solid after lyophilization. $^1$H NMR (CD$_3$CN, 500 MHz) δ 8.05 (d, 8.9 Hz, 1H), 6.95 (dd, 2.0 & 8.7 Hz, 1H), 6.86 (br s, 1H), 6.68 (br s, 1H), 3.86 (s, 3H), 3.79 (heptet, 6.9 Hz, 1H), 1.31 (s, 9H), 1.20 (d, 6.9 Hz, 6H).
LC-MS: 2.99 min. (m/Z=397.1, 419).

Functional Assays

A. Maxi-K Channel

The activity of the compounds can also be quantified by the following assay.

The identification of inhibitors of the Maxi-K channel is based on the ability of expressed Maxi-K channels to set cellular resting potential after transfection of both alpha and beta1 subunits of the channel in HEK-293 cells and after being incubated with potassium channel blockers that selectively eliminate the endogenous potassium conductances of HEK-293 cells. In the absence of maxi-K channel inhibitors, the transfected HEK-293 cells display a hyperpolarized membrane potential, negative inside, close to $E_K$ (−80 mV) which is a consequence of the activity of the maxi-K channel. Blockade of the Maxi-K channel by incubation with maxi-K channel blockers will cause cell depolarization. Changes in membrane potential can be determined with voltage-sensitive fluorescence resonance energy transfer (FRET) dye pairs that use two components, a donor coumarin (CC$_2$DMPE) and an acceptor oxanol (DiSBAC$_2$(3)).

Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization, which determines if a test compound actively blocks the maxi-K channel.

The HEK-293 cells were obtained from the American Type Culture Collection, 12301 Parklawn Drive, Rockville, Md., 20852 under accession number ATCC CRL-1573. Any restrictions relating to public access to the microorganism shall be irrevocably removed upon patent issuance.

Transfection of the alpha and beta1 subunits of the maxi-K channel in HEK-293 cells was carried out as follows: HEK-293 cells were plated in 100 mm tissue culture treated dishes at a density of 3×10$^6$ cells per dish, and a total of five dishes were prepared. Cells were grown in a medium consisting of Dulbecco's Modified Eagle Medium (DMEM) supplemented with 10% Fetal Bovine serum, 1×L-Glutamine, and 1× Penicillin/Streptomycin, at 37° C., 10% CO$_2$. For transfection with Maxi-K hα(pCIneo) and Maxi-K hβ1(pIRESpuro) DNAs, 150 μl FuGENE6™ was added dropwise into 10 ml of serum free/phenol-red free DMEM and allowed to incubate at room temperature for 5 minutes. Then, the FuGENE6™ solution was added dropwise to a DNA solution containing 25 μg of each plasmid DNA, and incubated at room temperature for 30 minutes. After the incubation period, 2 ml of the FuGENE6 ™/DNA solution was added dropwise to each plate of cells and the cells were allowed to grow two days under the same conditions as described above. At the end of the second day, cells were put under selection media which consisted of DMEM supplemented with both 600 μg/nm G418 and 0.75 μg/ml puromycin. Cells were grown until separate colonies were formed. Five colonies were collected and transferred to a 6 well tissue culture treated dish. A total of 75 colonies were collected. Cells were allowed to grow until a confluent monolayer was obtained. Cells were then tested for the presence of maxi-K channel alpha and beta1 subunits using an assay that monitors binding of $^{125}$I-iberiotoxin-D19Y/Y36F to the channel. Cells expressing $^{125}$I-iberiotoxin-D19Y/Y36F binding activity were then evaluated in a functional assay that monitors the capability of maxi-K channels to control the membrane potential of transfected HEK-293 cells using fluorescence resonance energy transfer (FRET) ABS technology with a VIPR instrument. The colony giving the largest signal to noise ratio was subjected to limiting dilution. For this, cells were resuspended at approximately 5 cells/ml, and 200 μl were plated in individual wells in a 96 well tissue culture treated plate, to add ca. one cell per well. A total of two 96 well plates were made. When a confluent monolayer was formed, the cells were transferred to 6 well tissue culture treated plates. A total of 62 wells were transferred. When a confluent monolayer was obtained, cells were tested using the FRET-functional assay. Transfected cells giving the best signal to noise ratio were identified and used in subsequent functional assays.

For Functional Assays:

The transfected cells (2E+06 Cells/mL) are then plated on 96-well poly-D-lysine plates at a density of about 100,000 cells/well and incubated for about 16 to about 24 hours. The medium is aspirated of the cells and the cells washed one time with 100 μl of Dulbecco's phosphate buffered saline (D-PBS). One hundred microliters of about 9 μM coumarin (CC$_2$DMPE)-0.02% pluronic-127 in D-PBS per well is added and the wells are incubated in the dark for about 30 minutes. The cells are washed two times with 100 μl of Dulbecco's phosphate-buffered saline and 100 μl of about 4.5 μM of oxanol (DiSBAC$_2$(3)) in (mM) 140 NaCl, 0.1 KCl, 2 CaCl$_2$, 1 MgCl$_2$, 20 Hepes-NaOH, pH 7.4, 10 glucose is added. Three micromolar of an inhibitor of endogenous potassium conductance of HEK-293 cells is added. A maxi-K channel blocker is added (about 0.01 micromolar to about 10 micromolar) and the cells are incubated at room temperature in the dark for about 30 minutes.

The plates are loaded into a voltage/ion probe reader (VIPR) instrument, and the fluorescence emission of both $CC_2DMPE$ and $DiSBAC_2(3)$ are recorded for 10 sec. At this point, 100 µL of high-potassium solution (mM): 140 KCl, 2 $CaCl_2$, 1 $MgCl_2$, 20 Hepes-KOH, pH 7.4, 10 glucose are added and the fluorescence emission of both dyes recorded for an additional 10 sec. The ratio $CC_2DMPE/DiSBAC_2(3)$, before addition of high-potassium solution equals 1. In the absence of maxi-K channel inhibitor, the ratio after addition of high-potassium solution varies between 1.65-2.0. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with $IC_{50}$'s in the range of about 1 nM to about 20 µM, more preferably from about 10 nM to about 500 nM.

B. Electrophysiological Assays of Compound Effects on High-conductance Calcium-activated Potassium Channels Methods:

Patch clamp recordings of currents flowing through large-conductance calcium-activated potassium (maxi-K) channels were made from membrane patches excised from CHO cells constitutively expressing the α-subunit of the maxi-K channel or HEK293 cells constitutively expressing both α- and β-subunits using conventional techniques (Hamill et al., 1981, Pfluigers Archiv. 391, 85-100) at room temperature. Glass capillary tubing (Garner #7052 or Drummond custom borosilicate glass 1-014-1320) was pulled in two stages to yield micropipettes with tip diameters of approximately 1-2 microns. Pipettes were typically filled with solutions containing (mM): 150 KCl, 10 Hepes (4-(2-hydroxyethyl)-1-piperazine methanesulfonic acid), 1 Mg, 0.01 Ca, and adjusted to pH 7.20 with KOH. After forming a high resistance ($>10^9$ ohms) seal between the plasma membrane and the pipette, the pipette was withdrawn from the cell, forming an excised inside-out membrane patch. The patch was excised into a bath solution containing (mM): 150 KCl, 10 Hepes, 5 EGTA (ethylene glycol bis(β-aminoethyl ether)-N,N,N',N'-tetraacetic acid), sufficient Ca to yield a free Ca concentration of 1-5 µM, and the pH was adjusted to 7.2 with KOH. For example, 4.193 mM Ca was added to give a free concentration of 1 µM at 22° C. An EPC9 amplifier (HEKA Elektronic, Lambrect, Germany) was used to control the voltage and to measure the currents flowing across the membrane patch. The input to the headstage was connected to the pipette solution with a Ag/AgCl wire, and the amplifier ground was connected to the bath solution with a Ag/AgCl wire covered with a tube filled with agar dissolved in 0.2 M KCl. The identity of maxi-K currents was confirmed by the sensitivity of channel open probability to membrane potential and intracellular calcium concentration.

Data acquisition was controlled by PULSE software (HEKA Elektronic) and stored on the hard drive of a Macintosh computer (Apple Computers) for later analysis using PULSEFIT (HEKA Elektronic) and Igor (Wavemetrics, Oswego, Oreg.) software.

Results

The effects of the compounds of the present invention on maxi-K channels was examined in excised inside-out membrane patches with constant superfusion of bath solution. The membrane potential was held at −80 mV and brief (100-200 ms) voltage steps to positive membrane potentials (typically +50 mV) were applied once per 15 seconds to transiently open maxi-K channels. As a positive control in each experiment, maxi-K currents were eliminated at pulse potentials after the patch was transiently exposed to a low concentration of calcium (<10 nM) made by adding 1 mM EGTA to the standard bath solution with no added calcium. The fraction of channels blocked in each experiment was calculated from the reduction in peak current caused by application of the specified compound to the internal side of the membrane patch. Compound was applied until a steady state level of block was achieved. $K_I$ values for channel block were calculated by fitting the fractional block obtained at each compound concentration with a Hill equation. The $K_I$ values for channel block by the compounds described in the present invention range from 0.01 nM to greater than 10 µM.

What is claimed is:

1. A compound of the structural formula I:

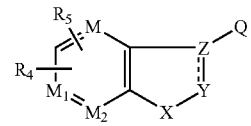

Formula I or a pharmaceutically acceptable salt, in vivo hydrolysable ester, enantiomer, diastereomer, geometric isomers or mixture thereof:

wherein,

M, M1, and M2, independently are CH;

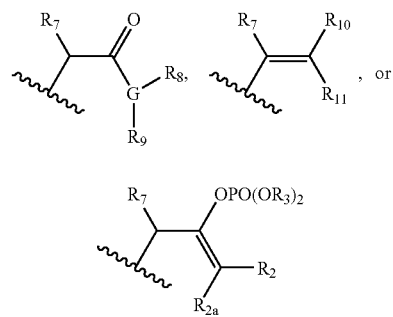

, or

Z represents N;

when Z is N then the bond between Y and Z is a single bond and between X and Y respectively represents: $CR_1$=N;

$R_1$ represents:

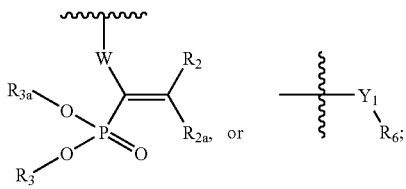

with the proviso that there is at least one enol phosphate group present on the compound, W represents —$(CHR_7)_p$—;

$Y_1$ represents —$(CH_2)_n$—, —$CO(CH_2)_n$—, —$SO_2$—, —O—, —S—, —CH(OR^)—, or CONR^;

R^ represents hydrogen, $C_{1-10}$ alkyl, —$(CH_2)_nC_{1-6}$ alkoxy, —$(CH_2)_nC_{3-8}$ cycloalkyl, —$(CH_2)_nC_{3-10}$ heterocyclyl, said alkyl, heterocyclyl, aryl or heteroaryl optionally substituted with 1-3 groups selected from $R^a$;

or, R^ and $R_6$ taken together with the intervening N atom of CONR' of $Y_1$ to form a 4-10 membered carbocyclic or heterocyclic ring or fused ring optionally interrupted by 1-3 atoms of O, S, C(O) or NR, and optionally having 1-5 double bonds, and optionally substituted by 1-3 groups selected from $R^a$;

G represents N, CRy, or O, wherein $R_8$ is absent when G is O;

$R_2$ and $R_{2a}$ independently represents hydrogen, $C_{1-10}$ alkyl, —$(CH_2)_nC_{3-8}$ cycloalkyl, —$(CH_2)_nC_{3-10}$ heterocyclyl, —$(CH_2)_nC_{6-10}$ aryl, —$(CH_2)_nC_{1-6}$ alkoxy, $CF_3$, nitro, OH, cyano or halogen, said alkyl, alkoxy, heterocyclyl, or aryl optionally substituted with 1-3 groups of $R^a$;

or, $R_2$ and $R_{2a}$ taken together with the intervening atom form a 4-10 membered cyclic carbon or heterocyclic ring or fused ring optionally interrupted by 1-2 atoms of O, S, C(O) or NR, and optionally having 1-5 double bonds, and optionally substituted by 1-3 groups selected from $R^a$;

$R_3$ and $R_{3a}$ independently represent hydrogen, $C_{1-10}$ alkyl, —$(CH_2)_nC_{3-10}$ heterocyclyl, —$(CH_2)_nC_{1-6}$ alkoxy, —$(CH_2)_nC_{6-10}$ aryl, said alkyl, alkoxy, heterocyclyl, or aryl optionally substituted with 1-3 groups of $R^a$;

$R_4$ and $R_5$ independently represent hydrogen, $C_{1-6}$ alkoxy, OH, $C_{1-6}$ alkyl, $C_{1-6}$ alkenyl, S(O)qR, COOR, COR, $SO_3H$, —$O(CH_2)_nN(R)_2$, —$O(CH_2)_nCO_2R$, —OPO$(OH)_2$, $CF_3$, $OCF_3$, —$N(R)_2$, nitro, cyano, $C_{1-6}$ alkylamino, or halogen;

$R_6$ represents hydrogen, $C_{1-10}$ alkyl, —$(CH_2)_nC_{6-10}$ aryl, —$NH(CH_2)_nC_{6-10}$ aryl, —$(CH_2)_nC_{5-10}$ heteroaryl, —$NH(CH_2)_nC_{5-10}$ heteroaryl, $(C_{6-10}$ aryl)O—, —$(CH_2)_nC_{3-10}$heterocyclyl, —$(CH_2)_nC_{3-10}$ cycloalkyl including fused rings, —COOR, —$C(O)CO_2R$, said aryl, heteroaryl, heterocyclyl, cycloalkyl, and alkyl optionally substituted with 1-3 groups selected from $R^a$ $R_7$ represents hydrogen, $C_{1-6}$ alkyl, —$(CH_2)_nCOOR$ or —$(CH_2)_nN(R)_2$, $R_8$ represents hydrogen, $C_{1-10}$ alkyl, $C_{1-6}$ alkylSR, —$(CH_2)_nO(CH_2)_mOR$, —$(CH_2)_nC_{1-6}$ alkoxy, —$(CH_2)_nC_{3-8}$ cycloalkyl, —$(CH_2)_nC_{3-10}$ heterocyclyl, —$(CH_2)_nC_{5-10}$ heteroaryl, —$N(R)_2$, —COOR, or —$(CH_2)_nC_{6-10}$ aryl, said alkyl, heterocyclyl, aryl or heteroaryl optionally substituted with 1-3 groups selected from $R^a$;

$R_9$ represents hydrogen, $C_{1-10}$ alkyl, —$(CH_2)_nC_{3-8}$ cycloalkyl, —$(CH_2)_nC_{3-10}$ heterocyclyl, —$(CH_2)_nC_{5-10}$ heteroaryl, —$(CH_2)_nCOOR$, —$(CH_2)_nC_{6-10}$ aryl, —$(CH_2)_nNHR_8$, —$(CH_2)_nN(R)_2$, —$(CH_2)_nN(R_8)_2$, —$(CH_2)_nNHCOOR$, —$(CH_2)_nN(R_8)CO_2R$, —$(CH_2)_n(R_8)COR$, —$(CH_2)_nNHCOR$, —$(CH_2)_nCONH(R_8)$, aryl, —$(CH_2)_nC_{1-6}$—OR, $CF_3$, —$(CH_2)_nSO_2R$, —$(CH_2)_nSO_2N(R)_2$, —$(CH_2)_nCON(R)_2$, —$(CH_2)_n$CONHC(R)_3, —$(CH_2)_nCONHC(R)_2CO_2R$, —$(CH_2)_n$ $COR_8$, nitro, cyano or halogen, said alkyl, alkoxy, heterocyclyl, aryl or heteroaryl optionally substituted with 1-3 groups of $R^a$;

or, when Q is N, $R_8$ and $R_9$ taken together with the intervening N atom form a 4-10 membered heterocyclic carbon ring optionally interrupted by 1-2 atoms of O, S, C(O) or NR, and optionally having 1-5 double bonds, and optionally substituted by 1-3 groups selected from $R^a$;

or when Q is CRy, $R_8$ and $R_9$ taken together with the intervening C atom form a 3-10 membered carbocyclic ring or fused ring optionally interrupted by 1-2 atoms of O, S, C(O) or NR, and optionally having 1-5 double bonds, and optionally substituted by 1-3 groups selected from $R^a$;

or or when Q is CRy, $R_8$ and $R_9$ taken together with the intervening CRy form a 5-12 membered fused ring optionally interrupted by 1-3 atoms of O, S, C(O) or NR, and optionally having 1-5 double bonds, and optionally substituted by 1-3 groups selected from $R^a$;

$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2$ $C_{6-10}$ aryl, $NO_2$, CN or —$C(O)N(R)_2$;

R, and Ry independently represent hydrogen, or $C_{1-6}$ alkyl;

$R^a$ represents F, Cl, Br, I, $CF_3$, $N(R)_2$, $NO_2$, CN, —$COR_8$, —$CONHR_8$, —$CON(R_8)_2$, —$O(CH_2)_nCOOR$, —$NH(CH_2)_nOR$, —COOR, —$OCF_3$, —NHCOR, —$SO_2R$, —$SO_2NR_2$, —SR, $(C_1-C_6$ alkyl)O—, —$(CH_2)_nO(CH_2)_mOR$, —$(CH_2)_nC_{1-6}$ alkoxy, (aryl)O—, —$(CH_2)_nOH$, $(C_1-C_6$ alkyl)$S(O)_m$—, $H_2N$—C(NH)—, $(C_1-C_6$ alkyl)C(O)—, $(C_1-C_6$ alkyl)OC(O)NH—, —$(C_1-C_6$ alkyl)$NR_w(CH_2)_nC_{3-10}$ heterocyclyl-$R_w$, —$(C_1-C_6$ alkyl)O$(CH_2)_nC_{3-10}$ heterocyclyl-$R_w$, —$(C_1-C_6$ alkyl)S$(CH_2)_nC_{3-10}$ heterocyclyl-$R_w$, —$(C_1-C_6$ alkyl)-$C_{3-10}$ heterocyclyl-$R_w$, —$(CH_2)_n$—$Z^1$—$C(=Z^2)N(R)_2$, —$(C_{2-6}$ alkenyl)$NR_w(CH_2)_nC_{3-10}$ heterocyclyl-$R_w$, —$(C_{2-6}$ alkenyl)O$(CH_2)_nC_{3-10}$ heterocyclyl-$R_w$, —$(C_{2-6}$ alkenyl) S$(CH_2)_nC_{3-10}$ heterocyclyl-$R_w$, —$(C_{2-6}$ alkenyl)-$C_{3-10}$ heterocyclyl-$R_w$, —$(C_{2-6}$ alkenyl)-$Z^1$—$C(=Z^2)N(R)_2$, —$(CH_2)_nSO_2R$, —$(CH_2)_nSO_3H$, —$(CH_2)_nPO(OR)_2$, —$(CH_2)_nOPO(OR)_2$, $C_{3-10}$cycloalkyl, $C_{6-10}$ aryl, $C_{3-10}$ heterocyclyl, $C_{2-6}$ alkenyl, and $C_1-C_{10}$ alkyl, said alkyl, alkenyl, alkoxy, heterocyclyl and aryl optionally substituted with 1-3 groups selected from $C_1-C_6$ alkyl, CN, $NO_2$, OH, $CON(R)_2$ and COOR;

$Z^1$ and $Z^2$ independently represents $NR_w$, O, $CH_2$, or S;

m is 0-3;

n is 0-3;

p is 0-1; and q is 0-2.

2. The compound according to claim 1 wherein Q is

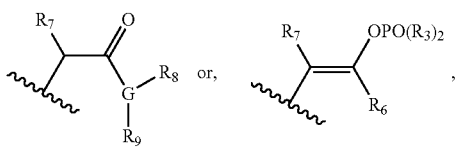

and G is N or CRy.

3. The compound according to claim 2 wherein $R_1$ is

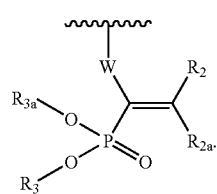

4. The compound according to claim 2 wherein $R_1$ is

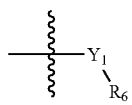

and $Y_1$ is —$(CH_2)_n$ or —$CO(CH_2)_n$.

5. A compound which is:
1-[1-(3,3-Dimethyl-2-oxobutyl)-6-methoxy-1H-indazol-3-yl]-2-methylprop-1-en-1-yl dimethyl phosphate;
1-[1-(3,3-Dimethyl-2-oxobutyl)-6-methoxy-1H-indazol-3-yl]-2-methylprop-1-en-1-yl dihydrogen phosphate;
1-(1-{2-[(3,3-Dimethylbutyl)(ethyl)amino]-2-oxoethyl}-6-methoxy-1H-indazol-3-yl)-2-methylprop-1-en-1-yl dihydrogen phosphate;
1-[1-(3,3-Dimethyl-2-oxopentyl)-6-methoxy-1H-indazol-3-yl]-2-methylprop-1-en-1-yl dihydrogen phosphate;
1-[1-(3,3-Dimethyl-2-oxopentyl)-6-methoxy-1H-indazol-3-yl]-2-methylprop-1-en-1-yl methyl hydrogen phosphate;
Cyclopentylidene[1-(3,3-dimethyl-2-oxobutyl)-6-methoxy-1H-indazol-3-yl]methyl dihydrogen phosphate;
Cyclopentylidene[1-(3,3-dimethyl-2-oxopentyl)-6-methoxy-1H-indazol-3-yl]methyl dihydrogen phosphate;
N,N-Dibutyl-2-(3-isobutyryl-6-methoxy-1H-indazol-1-yl)2-methylprop-1—en-1-yl dihydrogen phosphate;
N,N-Diisobutyl-2-(3-isobutyryl-6-methoxy-1H-indazol-1-yl)2 —methylprop-1-en-1-yl dihydrogen phosphate;
N-(Cyclopropylmethyl)-2-(3-isobutyryl-6-methoxy-1H-indazol-1-yl)2—methylprop-1-en-1-yl dihydrogen phosphate;
N-Cyclohexyl-N-ethyl-2-(3-isobutyryl-6-methoxy-1H-indazol-1-yl)2—methylprop-1en-1-yl dihydrogen phosphate;
2-(3-Isobutyryl-6-methoxy-1H-indazol-1-yl)-N,N-dipropyl2—methylprop-1-en-1-yl dihydrogen phosphate;
N-Butyl-N-ethyl-2-(3-isobutyryl-6-methoxy-1H-indazol-1-yl)2—methylprop-1-en-1-yl dihydrogen phosphate;
N-Ethyl-2-(3-isobutyryl-6-methoxy-1H-indazol-1-yl)-N-(3-methylbutyl)2—methylprop-1-en-1-yl dihydrogen phosphate;
N-Butyl-2-(3-isobutyryl-6-methoxy-1H-indazol-1-yl)-N-propyl2—methylprop-1-en-1yl dihydrogen phosphate;
2-(3-Isobutyryl-6-methoxy-1H-indazol-1-yl)-N,N-bis(3-methylbutyl)2—methylprop-1-en-1-yl dihydrogen phosphate;
1-(6-Methoxy-1-{2-[trans-octahydroisoquinolin-2(1H)-yl]-2-oxoethyl}-1H-indazol-3-yl) -2-methylprop-1-en-1yl dihydrogen phosphate;
1-(6-Methoxy-1-{2-[cis-octahydroisoquinolin-2(1H)-yl]-2-oxoethyl}-1H-indazol-3-yl) -2-methylprop-1-en1-yl dihydrogen phosphate;
N-(3,3-Dimethylbutyl)-2-(3-isobutyryl-6-methoxy-1H-indazol-1-yl)2—methylprop-1en-1-yl dihydrogen phosphate;
(Z)-1-tert-Butyl-2-{6-methoxy-3-[2-methyl-1-(phosphonooxy)prop-1-en-1-yl]-1H-indazol-1-yl}vinyl dihydrogen phosphate;
(Z)-1-tert-Butyl-2-(3-isobutyryl-6-methoxy-1H-indazol-1-yl)vinyl dihydrogen phosphate;

or a pharmaceutically acceptable salt, in vivo hydrolysable ester, enantiomer, diastereomer or mixture thereof.

6. A method for treating ocular hypertension or glaucoma comprising administration to a patient in need of such treatment a therapeutically effective amount of a compound of structural formula I of claim 1.

7. A composition comprising a compound of formula I of claim 1 and a pharmaceutically acceptable carrier.

8. The composition according to claim 7 wherein the compound of formula I is applied as a topical formulation, said topical formulation administered as a solution or suspension and optionally containing xanthan gum or gellan gum.

9. A composition according to claim 8 wherein one or more of an active ingredient belonging to the group consisting of: β-adrenergic blocking agent, parasympatho-mimetic agent, sympathomimetic agent, carbonic anhydrase inhibitor, EP4 agonist, a prostaglandin, hypotensive lipid, neuroprotectant, and/or 5-HT2 receptor agonist is optionally added.

10. A composition according to claim 9 wherein the β-adrenergic blocking agent is timolol, betaxolol, levobetaxolol, carteolol, or levobunolol; the parasympathomimetic agent is pilocarpine; the sympathomimetic agent is epinephrine, brimonidine, iopidine, clonidine, or para-aminoclonidine, the carbonic anhydrase inhibitor is dorzolamide, acetazolamide, metazolamide or brinzolamide; the prostaglandin is latanoprost, travaprost, unoprostone, rescula, or S1033, the hypotensive lipid is lumigan, the neuroprotectant is eliprodil, R-eliprodil or memantine; and the 5-HT2 receptor agonist is 1-(2-aminopropyl)-3-methyl-1H-imdazol-6-ol fumarate or 2-(3-chloro-6-methoxy-indazol-1-yl)-1-methyl-ethylamine.

* * * * *